(12) United States Patent
Solanki et al.

(10) Patent No.: US 11,754,479 B2
(45) Date of Patent: Sep. 12, 2023

(54) SYSTEM FOR TEAR ANALYSIS OF FILMS

(71) Applicant: Dow Global Technologies LLC, Midland, MI (US)

(72) Inventors: Sanjay C. Solanki, Midland, MI (US); Donald L. McCarty, II, Midland, MI (US); Robert A. Gunther, Midland, MI (US); Jin Wang, Midland, MI (US); Kyle A. Myers, Midland, MI (US); Scott J. Collick, Midland, MI (US)

(73) Assignee: Dow Global Technologies LLC, Midland, MI (US)

( * ) Notice: Subject to any disclaimer, the term of this patent is extended or adjusted under 35 U.S.C. 154(b) by 664 days.

(21) Appl. No.: 16/630,746

(22) PCT Filed: Apr. 30, 2018

(86) PCT No.: PCT/US2018/030210
§ 371 (c)(1),
(2) Date: Jan. 13, 2020

(87) PCT Pub. No.: WO2019/027518
PCT Pub. Date: Feb. 7, 2019

(65) Prior Publication Data
US 2020/0166442 A1    May 28, 2020

Related U.S. Application Data

(60) Provisional application No. 62/539,399, filed on Jul. 31, 2017.

(51) Int. Cl.
*G01N 3/08* (2006.01)
*G01N 33/44* (2006.01)
(Continued)

(52) U.S. Cl.
CPC ............... *G01N 3/08* (2013.01); *G01N 33/44* (2013.01); *G01N 33/346* (2013.01); *G01N 33/36* (2013.01); *G01N 2203/0282* (2013.01)

(58) Field of Classification Search
CPC ..... G01N 2203/006; G01N 2203/0003; G01N 2203/0206; G01N 2203/0278;
(Continued)

(56) References Cited

U.S. PATENT DOCUMENTS 2,340,401 A * 2/1944 Martin ..................... G01N 3/08
73/835
4,606,230 A * 8/1986 Scott ........................ G01N 3/08
73/826

(Continued)

FOREIGN PATENT DOCUMENTS

JP        755669 A     1/1974
JP      52136622 S    10/1977
(Continued)

OTHER PUBLICATIONS

Communication Pursuant to Article 94(3) EPC dated Feb. 2, 2021, pertaining to EP 18731549.4.
(Continued)

*Primary Examiner* — Harshad R Patel
*Assistant Examiner* — Gedeon M Kidanu
(74) *Attorney, Agent, or Firm* — Dinsmore & Shohl LLP

(57) ABSTRACT

A method and a system for analyzing a physical characteristic of a film sample are described herein. The system includes a material holder system configured to hold the film sample; and a tear analysis device configured to tear the film sample and measure a characteristic of the tear. The movable system is configured to move the film sample in the material holder system to the tear analysis device.

17 Claims, 17 Drawing Sheets

(51) Int. Cl.
*G01N 33/34* (2006.01)
*G01N 33/36* (2006.01)

(58) Field of Classification Search
CPC ... G01N 2203/0282; G01N 2203/0641; G01N 3/02; G01N 3/08; G01N 33/346; G01N 33/36; G01N 3/58; G01N 33/442; G01N 33/367; G01N 33/44
See application file for complete search history.

(56) References Cited

U.S. PATENT DOCUMENTS

| | | | |
|---|---|---|---|
| 4,708,381 A * | 11/1987 | Lundback | B65G 47/91 269/21 |
| 5,437,192 A * | 8/1995 | Kawamoto | G01N 33/367 73/159 |
| 6,139,889 A | 10/2000 | Guinee et al. | |
| 2010/0300195 A1 * | 12/2010 | Coulter | G01N 3/58 73/159 |
| 2013/0152706 A1 | 6/2013 | Nam et al. | |
| 2021/0078193 A1 | 3/2021 | McCarty, II et al. | |

FOREIGN PATENT DOCUMENTS

| | | |
|---|---|---|
| JP | H04125445 A | 4/1992 |
| JP | 5126705 A | 5/1993 |
| JP | 06313751 | 7/1996 |
| JP | 10253474 A | 9/1998 |
| JP | 2000111463 A | 4/2000 |
| JP | 2000352551 A | 12/2000 |
| JP | 3340197 B2 | 11/2002 |
| JP | 2002365187 A | 12/2002 |
| JP | 3196252 U | 2/2015 |
| KR | 20040054970 A | 6/2004 |
| KR | 20170030299 A | 3/2017 |

OTHER PUBLICATIONS

Communication Pursuant to Rules 161(1) and 162 EPC, dated Mar. 3, 12, 2020, pertaining to EP 18731549.4.
International Search Report and Written Opinion pertaining to PCT/US2018/030210, dated Aug. 10, 2018.
Japanese Office Action dated Apr. 5, 2022 pertaining to Japanese Patent Application No. 2020-503776.
Notice of Allowance dated Jan. 27, 2023, pertaining to U.S. Appl. No. 16/630,754 9 pages.
Shcherbina et al., "A Machine for Testing Thin Films with Automatic Recording of the Tensile Stress Diagram", Measurement Techniques, 1981, 1041-1042.
Shcherbina, M.E., "Installation for Thin Film Testing with Automatic Recording", Translated from Izmeritel'naya Tekhnika, 1989, 29-30.
International Search Report and Written Opinion pertaining to PCT/US2018/036700, dated Aug. 10, 2018.
Japanese Office Action, dated Apr. 5, 2022 pertaining to Japanese Patent Application No. 2020-504006.
Communication Pursuant to Article 94(3) EPC pertaining to EP 19735101.0, dated Feb. 2, 2022.
Korean non-final Office Action, dated May 24, 2022, pertaining to Korean Patent Application No. 10-2020-7005147.
International Preliminary Report on Patentability PCT/US2018/039700 dated Feb. 4, 2020.
International Preliminary Report on Patentability PCT/US2018/030210 dated Feb. 4, 2020.
International Search Report and Written Opinion pertaining to PCT/US2018/030261, dated Aug. 10, 2018.
Examination Report dated Feb. 10, 2022, pertaining to EP Patent Application No. 18731551.0, 6 pages.
Notice of Allowance dated May 13, 2022 pertaining to U.S. Appl. No. 16/630,709 (13 pages total).
Japanese Decision of Rejection dated Aug. 30, 2022, pertaining to Japanese Patent Application No. 2020-504006 3 pages.

* cited by examiner

SYSTEM FOR TEAR ANALYSIS OF FILMS

FIELD

The present invention relates to a system for tear analysis of a film or sheet of material.

INTRODUCTION

Characterizing physical properties of materials is useful in analyzing and improving chemical formulations employed in the production of the materials as well as in analyzing and improving processes of manufacturing the materials. Characterizing the physical properties may also help consumers determine the best product for their particular use case, as well as help researchers develop novel solutions for specific applications.

One of the useful physical properties of a material is determining tear strength of the material. A tear test provides insight into the ability of a material to resist tearing. For example, the tear test can be used for determining tear properties of thin films as thin films are often used in packaging applications. Tear testing can also be used for determining tear properties of polymeric samples such as adhesives, plaques, carpet fibers, non-woven fibers, etc., and in non-polymeric samples such as paper, cloth, foil, etc. The suitability of a material for an intended purpose may depend on the ability of the material to withstand or give way to tearing. In such instances, the chemical and physical characteristics of the material may affect the tear resistance of the material. The tear test usually involves performing a cut in a sample and tearing the sample along the cut. The force required to propagate the tear is measured and analyzed to determine the material's tear resistance.

The American Society for Testing and Materials (ASTM) has a set of standards that are widely used throughout the world for characterizing materials. Tear testing is a popular test that is performed frequently across the plastics industry. Currently, tear testing is performed using two methods: the Elmendorf Tear Test and the Trouser test. In both methods, a specimen is precut and a tear is propagated from the precut slit. The tests measure the average force required to propagate the tear through the specimen. According to known methods, a human operator is required for the preparation, analyzing, and disposal of the specimen. For example, according to known methods, a human operator is required to manually prepare the specimen, load and unload the specimen into the test equipment, and dispose of the torn specimen.

Therefore, a need remains for an automated system for analyzing the tear strength of films.

SUMMARY

It was determined that by using a system for tear analysis of films according to the present disclosure, the process can be automated and operated at high throughput.

According to an embodiment of the disclosure, a system for analyzing a physical characteristic of a film sample may include a material holder system configured to hold the film sample and a tear analysis device configured to tear the film sample and measure a characteristic of the tear. The movable system may be configured to move the film sample in the material holder system to the tear analysis device.

According to an embodiment of the disclosure, a method for analyzing a physical characteristic of a film sample may include holding the film sample by a material holder system connected to a movable system, moving the film sample using the movable system to a tear analysis device, and testing a physical characteristic of the film sample using the tear analysis device.

BRIEF DESCRIPTION OF THE DRAWINGS

The present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION

In industrial applications, the process of testing tear resistance of a thin film sample may be automated. The idea for automated tear analysis devices arises from a need for high throughput (HTP) testing in various industries. A higher rate of testing allows large amounts of data to be gathered relatively quickly and analyzed for trends, allowing more detailed studies to be conducted on areas of interest. One feature needed in the inception of an HTP testing setup is a continuous (or near continuous) operation. By allowing systems to run non-stop it increases the amount of testing performed. The system also allows an increase of the speed of a single test as compared to manual testing systems. This is accomplished using robotics to take the place of a human researcher or operator, as robots can run for longer periods of time without interruption. A second feature that may be used for increasing throughput of a system without sacrificing accuracy is to perform multiple tests in parallel. A third feature is that the system is repeatable and uniform as compared to human-based testing systems. Embodiments of the present disclosure employ one or both of these features to increase the number of film samples that can be tested.

In an embodiment of the present disclosure, HTP testing is achieved by using two robots working in parallel. For example, in an embodiment, a six-axis robot prepares the sample for testing while a Selective Compliance Assembly Robot Arm or Selective Compliance Articulated Robot Arm (SCARA) robot tears the films loaded in multiple tear stations. The film specimen may comprise polymeric samples such as adhesives, plaques, carpet fibers, non-woven fibers, etc., or non-polymeric samples such as paper, cloth, foil, etc.

Embodiments of the present disclosure can be integrated with the blown film fabrication line. Additionally, embodiments can be integrated into existing blown film labs. By being able to conduct tests automatically and relatively quickly, the labs would be able to clear out their backlog of tests using the present system.

Figure 1:
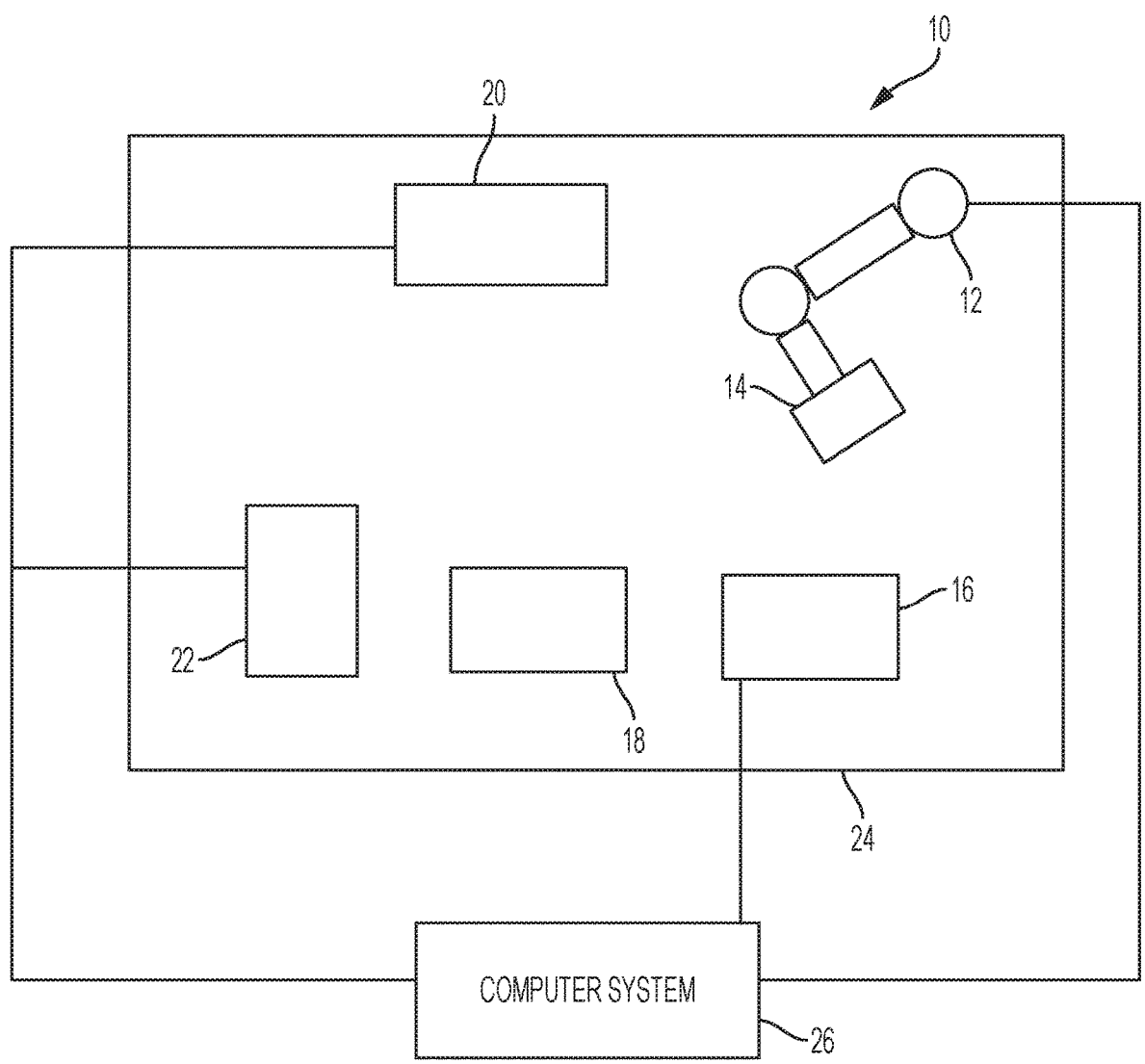
FIG. 1 shows a schematic diagram of a tear analysis system according to an embodiment of the present disclosure.

FIG. 1 shows a schematic diagram of the system according to an embodiment of the present disclosure. In an embodiment of the present disclosure, the tear analysis system 10 includes movable system, such as a robotic system 12, a material holder system 14, a thickness measurement system 16, a cutting device 18, a material image analyzer system 20, and tear analysis device 22. The robotic system 12, the material holder system 14, the thickness measurement system 16, the cutting device 18, the material image analyzer system 20, and/or the tear analysis device 22 can be provided on a work surface 24 or a common framework. The robotic system 12, the material holder system 14, the thickness measurement system 16, the cutting device 18, the material image analyzer system 20, and/or the tear analysis device 22 can be controlled using computer system 26.

Figure 2:
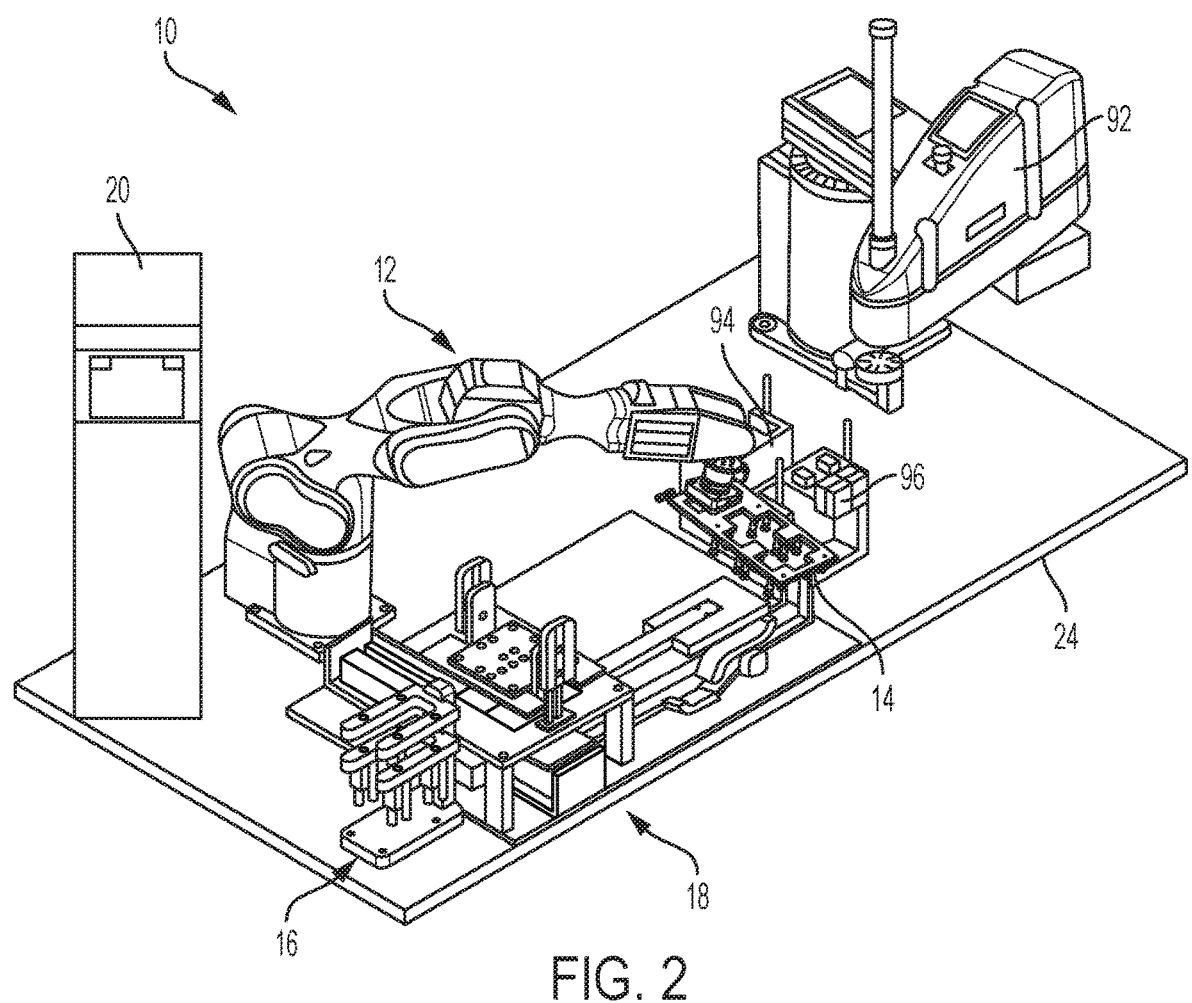
FIG. 2 shows a three-dimensional perspective view of a tear analysis system according to an embodiment of the present disclosure.

FIG. 2 shows a three-dimensional perspective view of the tear analysis system 10 according to the present disclosure. As can be seen in FIG. 2, the tear analysis device may comprise a tear robot 92 and fixed clamp stations 96 for performing a tear test on a film specimen, as will be described in more detail below. The tear analysis system 10 may include a delivery system. The delivery system may include trays which deliver samples to the work surface 24 for testing with the tear analysis system 10. The delivery system may deliver a film sample 66 (FIG. 7) to a location in front of the tear analysis system 10 where the robotic system 12 and material holder system 14 may retrieve the film sample from the tray and proceed through the steps of the testing procedure described herein.

Figure 3:
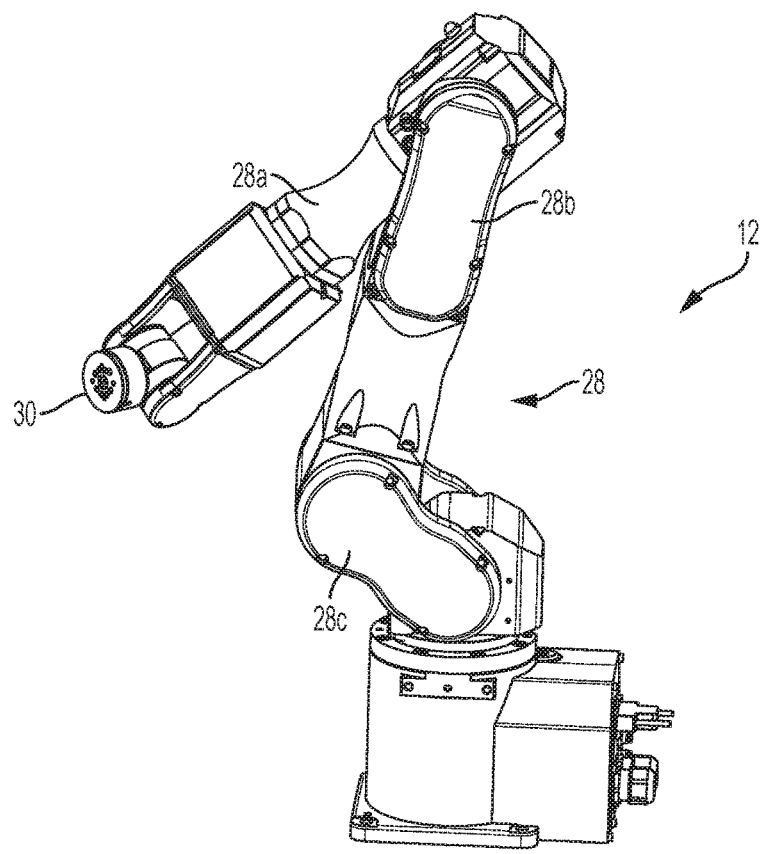
FIG. 3 shows a three-dimensional perspective view of a robotic system, according to an embodiment of the present disclosure.

FIG. 3 shows a three-dimensional perspective view of the robotic system 12, according to an embodiment of the present disclosure. In an embodiment, the robotic system 12 is a six-axis robotic arm system such as Epson C4 robot made by Epson Corporation. The robotic system 12 is configured to move a film sample or a film specimen (for example, a film) to be analyzed or tested between stations provided on the work surface 24. The robotic system 12 may comprise an articulating arm comprising articulating sections 28a, 28b, 28c. The articulating arm 28 may be capable of moving the material holder system 14 in all planes and directions and at any angle. The robotic system 12 may further have an adapter plate 30 attached to one of the articulating sections, such as articulating section 28a. The robotic system 12 may be manipulated by user input on the computer system 26 or alternatively be a preset program on the computer system 26.

Although a six-axis robotic arm system 12 is described, the robotic system 12 may be any system capable of being connected to the material holder system 14 and capable of moving film in multiple planes around the work surface 24. The robotic system 12 may be any articulating arm robot.

Figure 4:
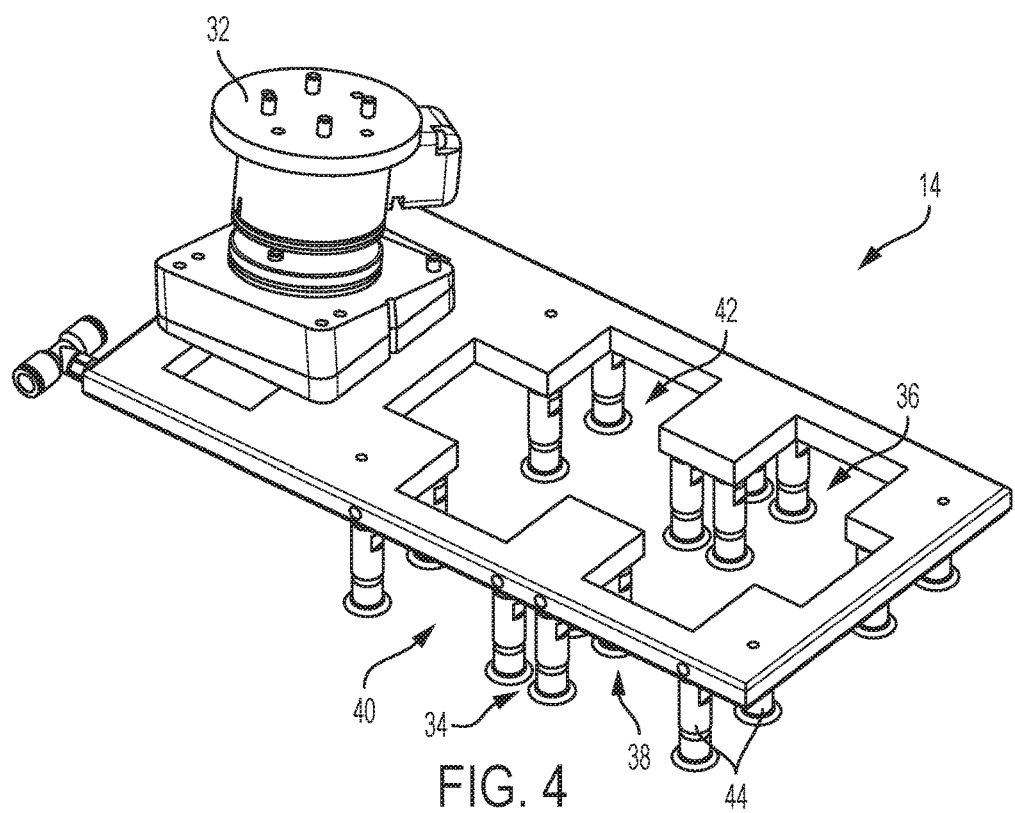
FIG. 4 shows a three-dimensional perspective view of a material holder system, according to an embodiment of the present disclosure.

FIG. 4 shows a three-dimensional perspective view of the material holder system 14, according to an embodiment of the present disclosure. The material holder system 14 is configured to hold and move film. The material holder system 14 may attach to the robotic system 12 with an adapter plate 32. The adapter plate 32 may attach to the adapter plate 30 of the robotic system 12, for example, using fasteners. When attached, the adapter plate 30 may transmit rotational, longitudinal, and angular motion from the articulating arm 28 to the material holder system 14. In an embodiment, the material holder system includes a vacuum suction system 34 adapted to hold the film through vacuum suction. In an embodiment, the vacuum suction system 34 includes four sets 36, 38, 40, and 42 of vacuum cups 44. Each set may include four vacuum cups 44. This allows for the material holder system 14 to handle either a single film sample of dimension 6"×6" (152 mm×152 mm), or four film specimens of size 3"×3" (76 mm×76 mm). One of ordinary skill in the art will recognize that when a 6"×6" (152 mm×152 mm) film sample is handled by the material holder system 14, all sixteen vacuum cups 44 can be employed to hold and move the film sample. When four film specimens of size 3"×3" (76 mm×76 mm) are handled by the material holder system 14, each set 36, 38, 40, and 42 of vacuum cups 44 can hold and move a respective film specimen. That is, the four vacuum cups 44 which make up set 36 can hold and move a single film specimen of size 3"×3" (76 mm×76 mm) and likewise for each of sets 38, 40, and 42. The material holder system 14 may hold and move the four film specimens simultaneously. Although sixteen vacuum cups 44 are described and shown, any number of vacuum cups may be used to hold and move the film specimen(s) through the testing process. Although the material holder system 14 was described with relation to manipulating a single 6"×6" (152 mm×152 mm) film sample and four 3"×3" (76 mm×76 mm)

film specimens, it is to be understood that more or less film specimens of different sizes and shapes may be held by the material holder system 14. That is, the film need not be 6"×6" (152 mm×152 mm) or 3"×3" (76 mm×76 mm), but could be any size, shape, or quantity of which testing is required.

Although vacuum cups are described herein as being used to hold the film, other mechanisms or systems can also be used to hold the film depending on the type of material. For example, the vacuum cups may be suited for holding non-porous and relatively light samples, such as various plastics and polymer materials. Therefore, if, for example, porous materials are used, then the vacuum cups may be replaced by other holding mechanisms such as magnets, clips, or other type of gripper.

Figure 5:
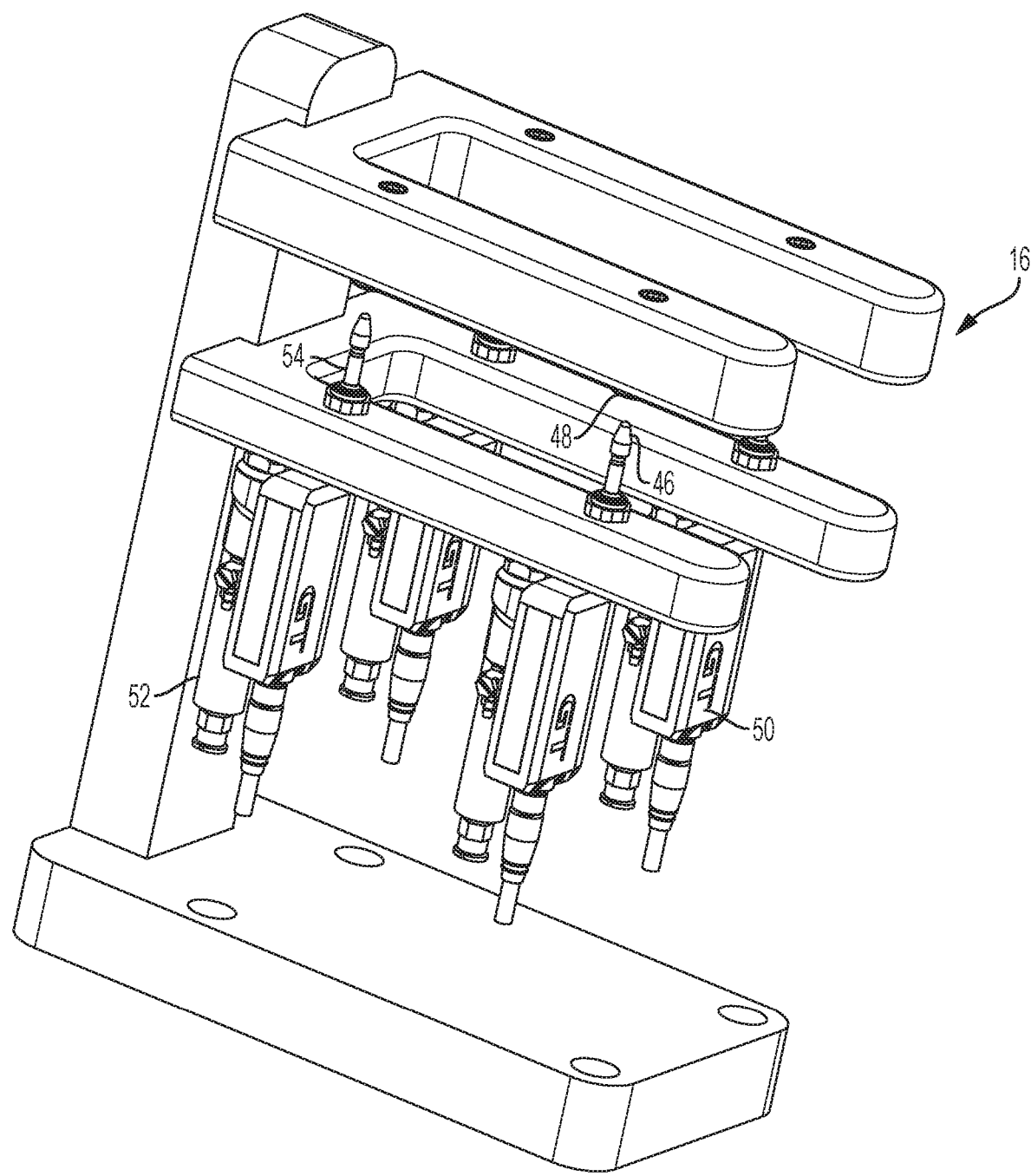
FIG. 5 shows a three-dimensional perspective view of components of a thickness measurement system, according to an embodiment of the present disclosure.

FIG. 5 shows a three-dimensional perspective view of the components of the thickness measurement system 16, according to an embodiment of the present disclosure. The thickness measurement system 16 may measure the thickness of the film specimen at the center of each film specimen to be cut therefrom, as prescribed in ASTM standard D5947. The thickness measurement system 16 is configured to measure a thickness of the film in a wide range of thicknesses, for example between 0.5 mil to 10 mil (0.0127 mm to 0.254 mm). The thickness measurement system 16 is configured to measure a thickness of the film using a contact plate and a probe. The contact plate and the probe are generally flat and contact the film on opposing surfaces 48 and 46, respectively, and the thickness of the film is measured as the distance between the contact plate and the probe. The surface 48 of the contact plate and the surface 46 of the probe is sufficient to avoid puncturing the film sample during the measurement. For example, the contact surfaces 46 and 48 can be configured to be used for materials that are flexible and pliable. The contact surfaces 46 and 48 can also be configured to measure a thickness of more rigid samples.

As can be seen in FIG. 5, the thickness measurement system 16 may comprise four first contact surfaces 46 and four second contact surfaces 48. The thickness measurement system 16 may comprise four sensors 50 to measure the thickness in an area which corresponds to each of the four film specimens to be cut therefrom. The sensors 50 can be mounted 3" (76 mm) apart and the 6"×6" (152 mm×152 mm) film sample can be inserted between the contact surfaces 46 and 48. The thickness may be measured at four distinct points. Each of the four thickness measurements can correspond to the thickness of one of the 3"×3" (76 mm×76 mm) film specimens. Alternatively, more or fewer contact surfaces 46 and 48 and sensors 50 may be provided. The number of contact surfaces 46 and 48 and sensors 50 provided may correspond to the number or the size of the film specimens to be tested. Alternatively, film samples sized other than 6"×6" (152 mm×152 mm) and cut film specimens sized other than 3"×3" (76 mm×76 mm) may be tested by the thickness measurement system 16.

The sensors 50 can comprise high-accuracy digital contact sensors 50 (for example, Keyence GT2 Series from Keyence Company). The sensors 50 are used to measure the thickness of the film to an accuracy of 1 micron. The sensors 50 are selected for their accuracy. Each first contact surface 46 may be mechanically linked to a corresponding sensor 50 by a shaft 54. The robotic system 12 and material holder system 14 may move the film sample such that each film specimen to be cut therefrom is located between the respective first contact surface 46 and second contact surface 48. Once the film sample is in place between the respective first contact surface 46 and second contact surface 48, pressurized air from air-pressure systems 52 may be applied to the shafts 54. The air-pressure systems 52 may extend the shaft 54 linked to each first contact surface 46 such that the film sample touches and is held between the respective first contact surface 46 and second contact surface 48. The sensor 50 may measure the distance between the extended first contact surface 46 and the second contact surface 48 to measure the thickness of the film sample.

Although a mechanical type thickness measurement system 16 is described and used, other types of thickness measuring systems can also be employed. For example, in another embodiment, the thickness measurement system 16 includes laser distance measuring sensors adapted to determine the thickness using laser beams. Also considered are confocal lens, dual laser thickness analyzers, and capacitive measurement methods.

Figure 6:
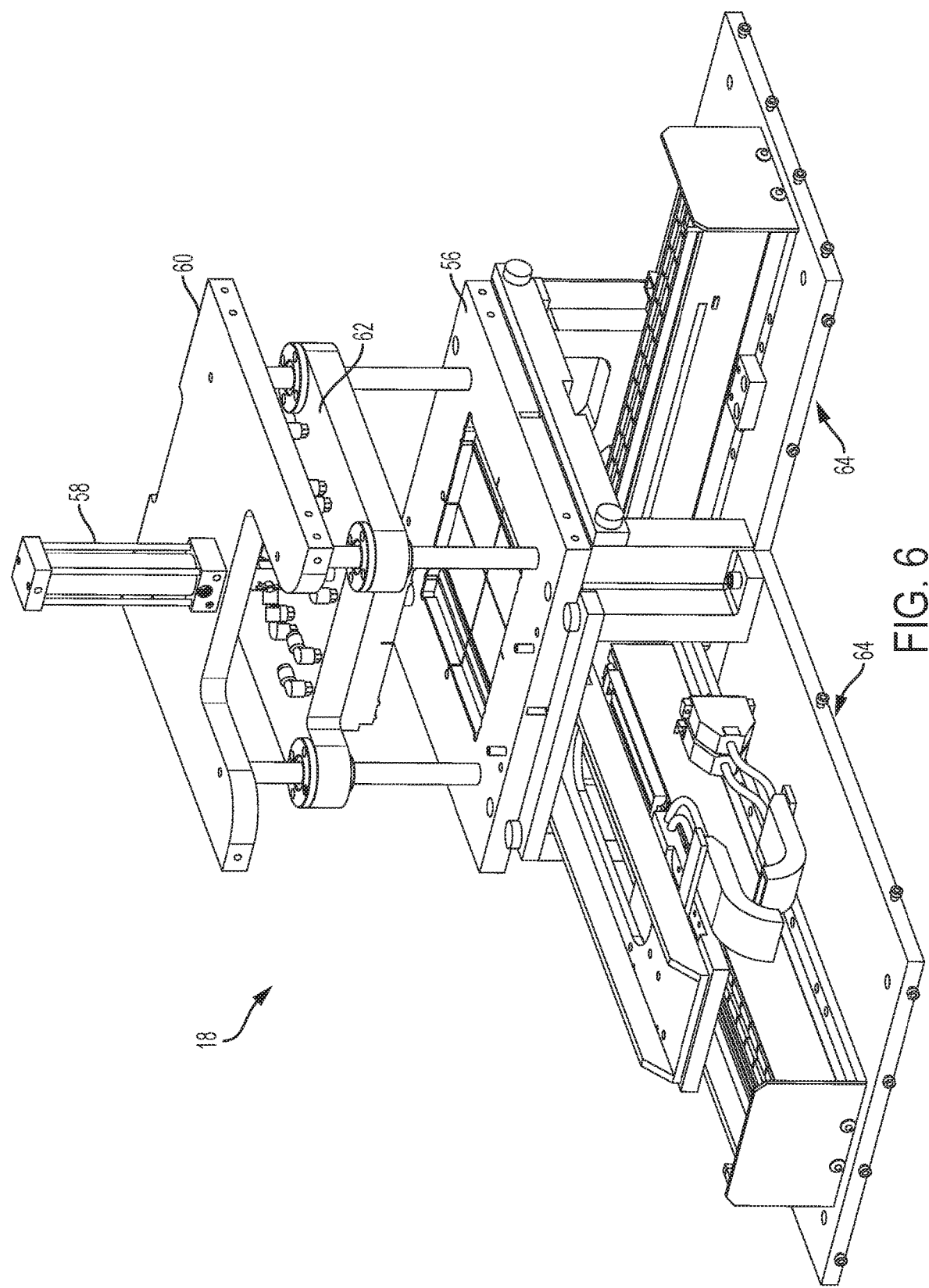
FIG. 6 shows a three-dimensional perspective view of components of a cutting device, according to an embodiment of the present disclosure.
Figure 7:
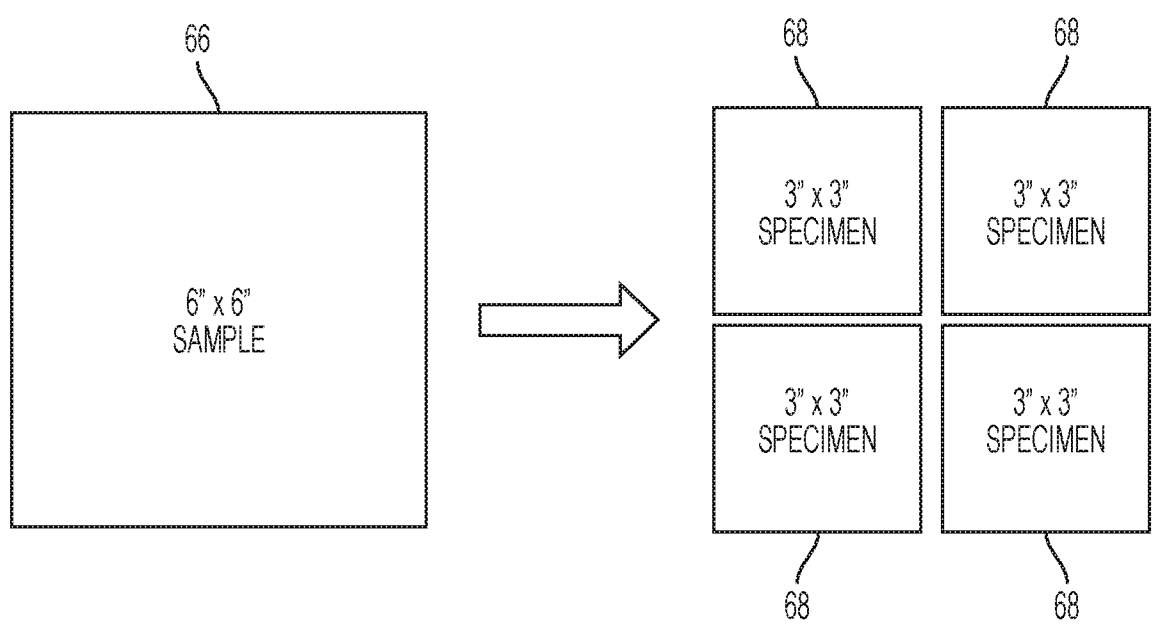
FIG. 7 shows a top view of a piece of film specimen before and after being cut with a cutting device, according to an embodiment of the present disclosure.

FIG. 6 shows a three-dimensional perspective view of the components of the cutting device 18, according to an embodiment of the present disclosure. For clarity of the description, the term "film sample" refers to a film material being tested in the tear analysis system 10 prior to the film material being cut with cutting device 18 and the term "film specimen" refers to the "film sample" which has been cut to a smaller size by the cutting device 18. With reference to FIG. 7, the cutting device 18 can be designed to cut a 6"×6" (152 mm×152 mm) square film sample 66 into four film specimens 68 each of size 3"×3" (76 mm×76 mm). Alternative starting and end sizes and shapes are possible. As shown in FIG. 6, the cutting device 18 may include two linear actuators, such as linear motors 64 positioned perpendicular to each other, although other angular relationships may be provided. Each linear motor 64 can drive a blade 70 (see FIGS. 8A, 8B). The cutting device 18 may include a film support plate 56 and a pressure plate 62. The cutting device 18 may also include a pneumatic cylinder 58 mounted to a top plate 60. The output of the pneumatic cylinder 58 can be fixed to the pressure plate 62. Accordingly, the pneumatic cylinder 58 can drive the upward and downward motion of the pressure plate 62 with respect to the film support plate 56. The uncut film sample may be inserted between the pressure plate 62 and film support plate 56 by the material holder system 14. Vacuum cups 82 (FIG. 10) on pressure plate 62 may be actuated to hold the film sample to the underside of the pressure plate 62. The vacuum cups 44 on the material holder system 14 may be deactivated and the material holder system 14 may be removed prior to actuating the pneumatic cylinder 58. The pressure plate 62 (operated by pneumatic cylinder 58) lowers the 6"×6" (152 mm×152 mm) film sample 66 onto the film support plate 56. According to an embodiment, the linear motors 64 alternately move the blades 70 laterally through the film sample to cut the 6"×6" (152 mm×152 mm) film sample 66 into four film specimens 68 of size 3"×3" (76 mm×76 mm). Although described with the pressure plate 62 holding the film sample 66 and cut film specimens 68, it is to be understood that the film support plate 56 may alternatively hold the film sample 66 prior to the pressure plate 62 being lowered by the pneumatic cylinder 58.

Figure 8A:
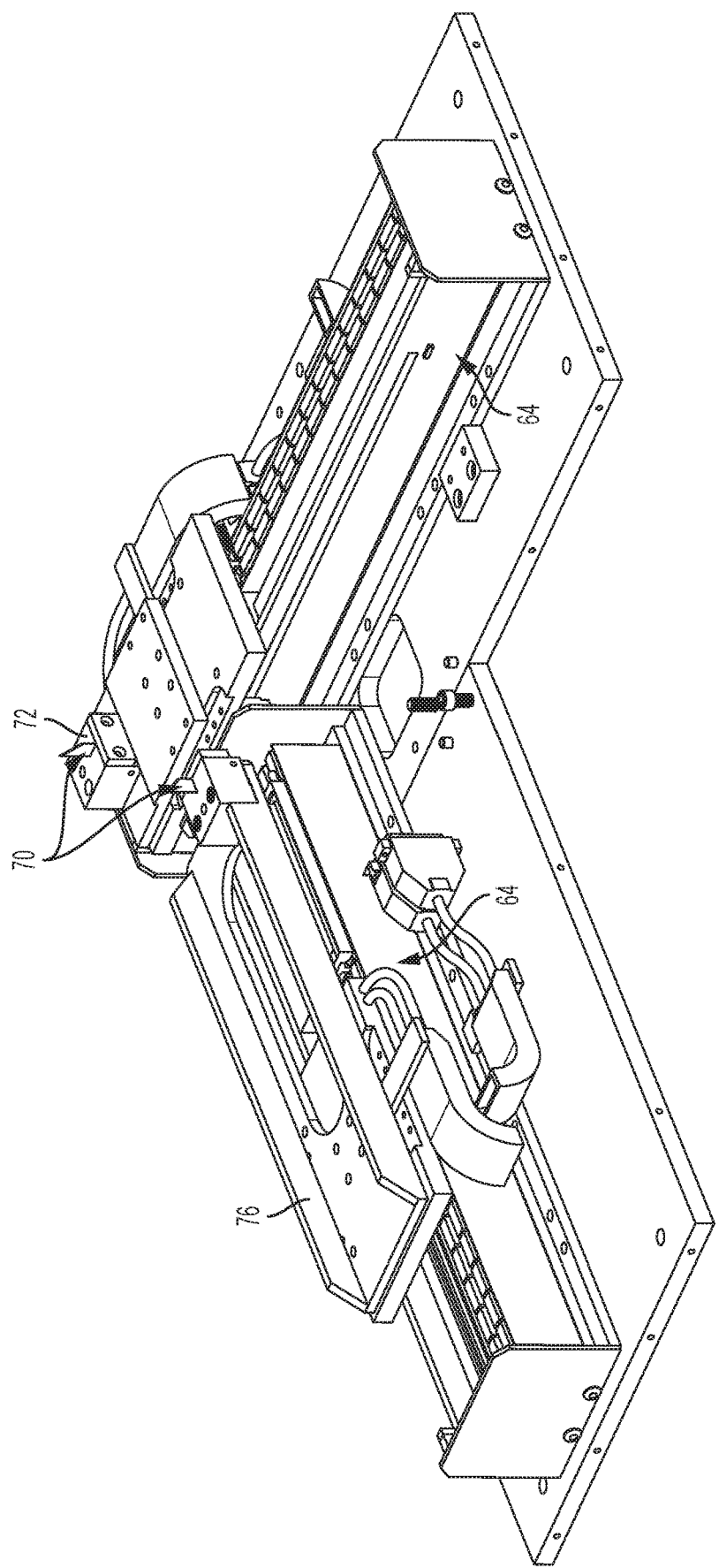
FIG. 8A shows a three-dimensional perspective view of components of a cutting device, according to an embodiment of the present disclosure.
Figure 8B:
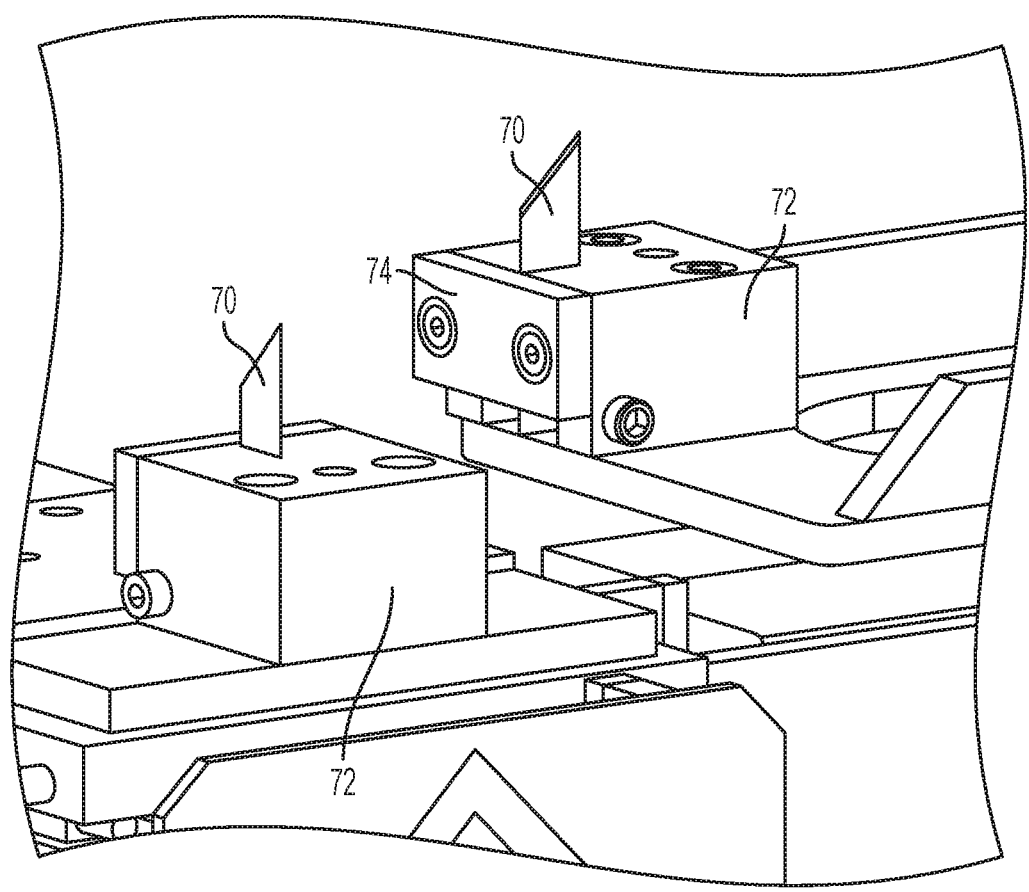
FIG. 8B shows a three-dimensional perspective view of components of a cutting device, according to an embodiment of the present disclosure.

Referring to FIGS. 8A and 8B, the blade 70 may be attached to the linear motor 64 by a block 72 attached to a sled 76. The sled 76 may be adapted to be actuated by the linear motor 64 such that it moves sled 76, block 72, and thus blades 70 in a linear direction. The blades 70 can move in directions perpendicular to one another. After a first blade 70 has been extended along the film sample and retracted, a second blade 70 can similarly cut the film sample at 90 degrees to the first cut. In an embodiment, the linear motors 64 are manufactured by Aerotech Corporation from Pittsburgh, Pa. In another embodiment, the linear motors 64 are manufactured by ETEL Corporation. In another embodiment, instead of linear motors, the blades 70 are driven by a rotational actuator or a hydraulic or pneumatic actuator. As can be seen in FIG. 8B, the blades 70 are secured by set screws (not labeled) in the block 72 to keep the blade from rising. To remove the blade 70 (such as for repair, cleaning, or replacement), the set screw is removed and the blade 70 can be lifted from the block 72. A front face plate 74 is also provide and serves to maintain the position of the blade 70 during travel. In another embodiment, a single blade 70 and linear motor 64 mounted on a rotatable table can be used to make the two perpendicular cuts into the film sample 66. In one instance, the linear motor 64 moves the blade at from 1 m/s to 4 m/s (3.3 ft/s to 13.1 ft/s).

Figure 9:
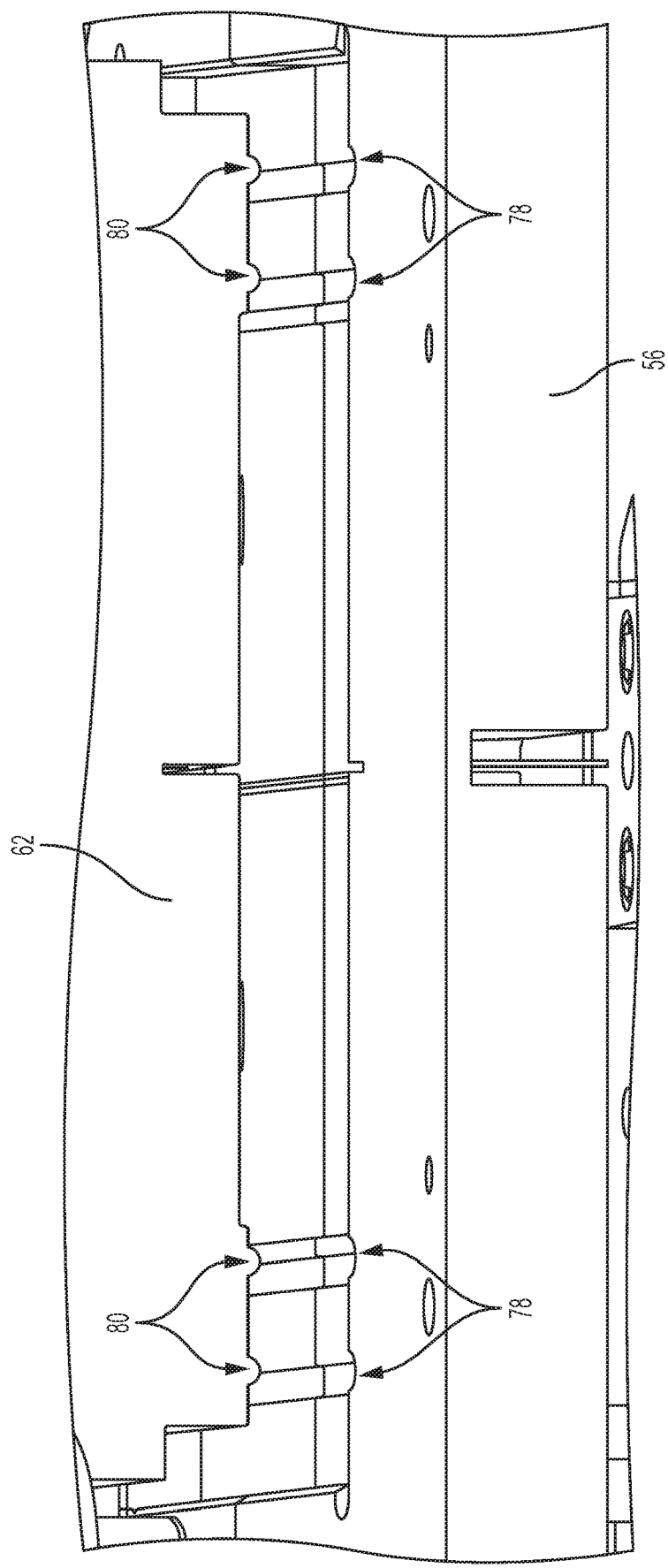
FIG. 9 shows a three-dimensional perspective view of components of a cutting device, according to an embodiment of the present disclosure.

FIG. 9 shows a three-dimensional perspective view of the film support plate 56 and pressure plate 62 of the cutting device 18, according to an embodiment of the present disclosure. Grooves 78 are milled into the film support plate 56 and tongues 80 are patterned into the pressure plate 62. The tongue 80 and groove 78 pattern extends along one direction. Thus, one of the blades 70 may cut parallel to the tongue 80 and groove 78 pattern while the other blade 70 may cut perpendicular to the tongue 80 and groove 78 pattern. The tongue 80 and groove 78 pattern is used to hold the film sample taut and in position while cutting. As the tongues 80 move downward and mate with the corresponding grooves 78, the film sample is pushed downward into the grooves 78. The effect of this being that the film sample becomes taut in the areas spanning mating tongues and grooves, and is held in place during cutting by blade 70. The location of the tongues 80 and grooves 78 may alternatively be reversed such that the tongues 80 are located on film support plate 56 and the grooves 78 are located on pressure plate 62.

Figure 10:
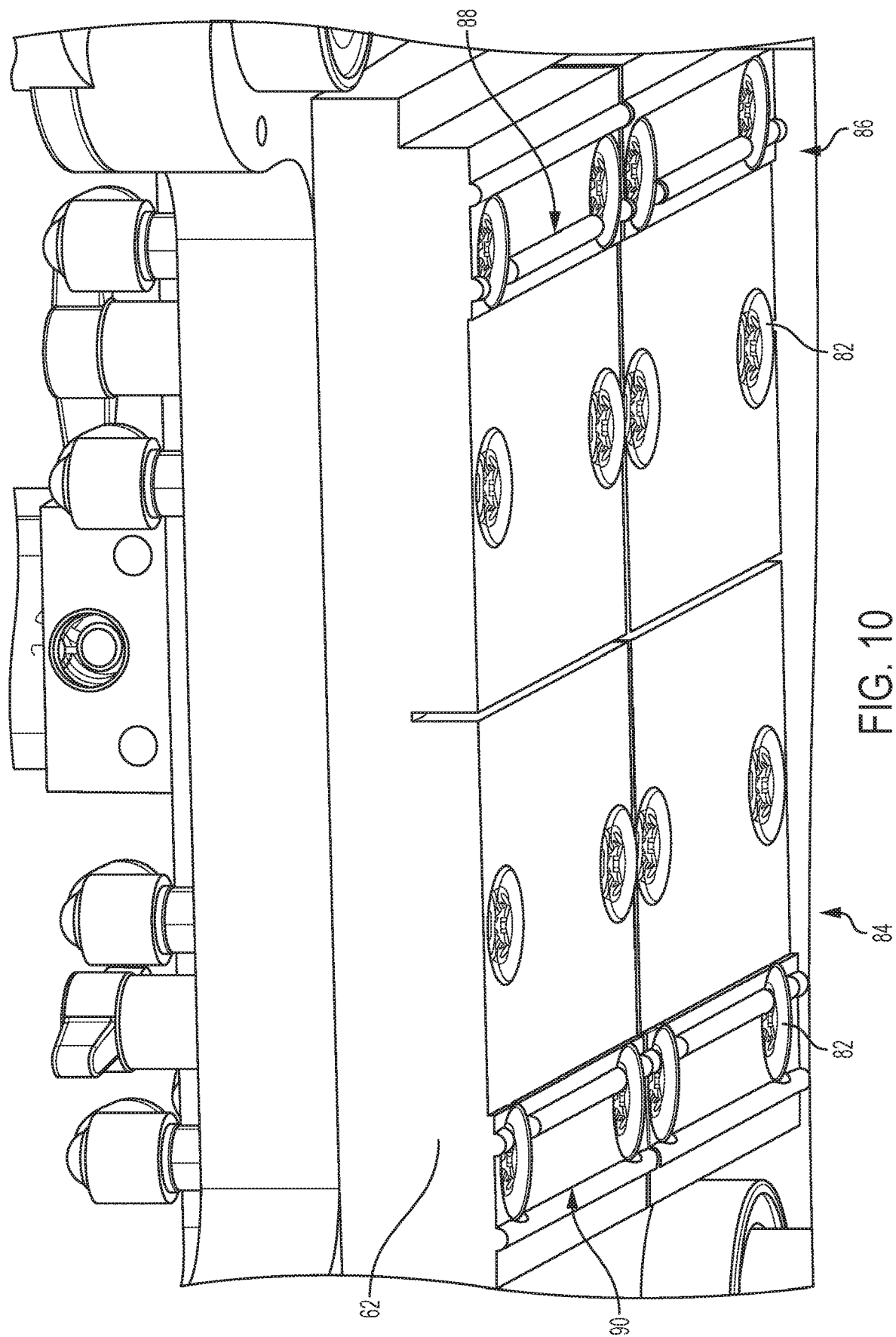
FIG. 10 shows a three-dimensional perspective view of components of a cutting device, according to an embodiment of the present disclosure.

FIG. 10 shows a three-dimensional perspective view of the pressure plate 62 of the cutting device 18, according to an embodiment of the present disclosure. The pressure plate 62 may include vacuum cups 82 located on the underside of the pressure plate 62. According to an embodiment, the vacuum cups 82 can be divided into four sets 84, 86, 88, and 90. After cutting, the vacuum supply to the vacuum cups 82 can be turned on for each cup, and the cut film specimens can be picked off the film support plate 56. The film specimens then rise with the pressure plate 62 as the pneumatic cylinder 58 lifts the pressure plate 62. An alternative cutting device 18 may be used, for example, the film sample may be cut by a user with a knife or scissors. The film sample may also be cut with other electric or automatic cutters, or mechanical cutters such as, for example, those in the style of swing arm paper cutters.

Figure 11:
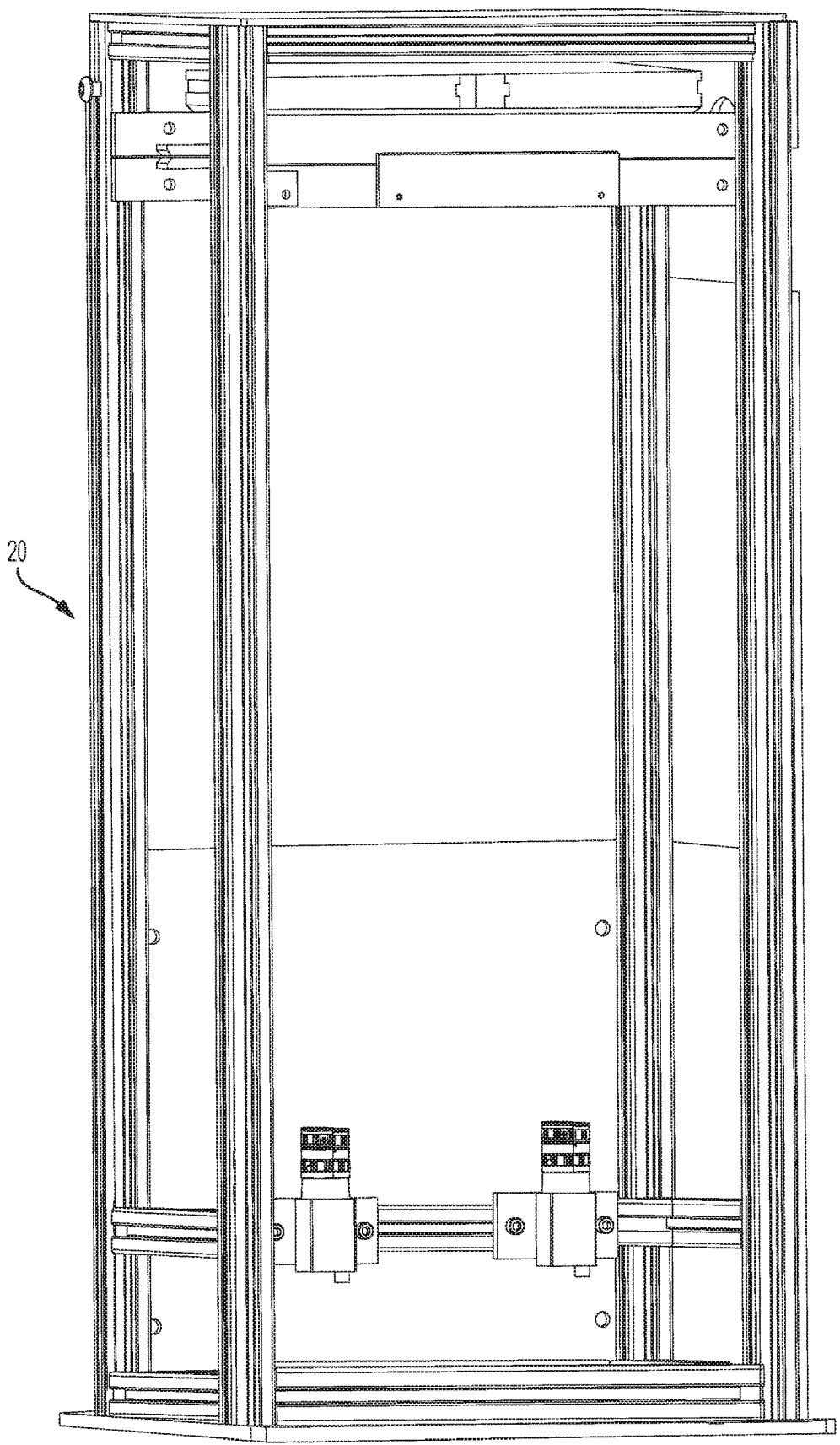
FIG. 11 shows a three-dimensional perspective view of an image analyzer system, according to an embodiment of the present disclosure.

FIG. 11 shows a three-dimensional perspective view of the material image analyzer system 20, according to an embodiment of the present disclosure. Following cutting, the film specimens may be moved by the robotic system 12 to the material image analyzer system 20. Although the process is described with material image analysis following cutting, it will be recognized that the order may be altered. According to embodiments, the order can be based, for example on proximity of the components on the work surface 24 to promote efficiency of the system. According to an embodiment, material image analysis may precede cutting. Thus, the film sample may be moved to the material image analyzer system 20 from the thickness measurement system 16 prior to being cut in the cutting device 18. According to an embodiment, material image analysis may precede thickness measurement.

According to embodiments, the material image analyzer system 20 is based on the principle of polarized light. The material image analyzer system 20 is configured to detect irregularities or defects in the film to be tested. A source of polarized light is used to illuminate the film within the material image analyzer system 20, while eliminating any ambient light. After the light passes through the film, it is captured by a camera fitted with a polarizing filter. A perfectly formed film specimen does not scatter the polarized light from the source thus resulting in a completely clear image. However, any imperfections/defects in the film specimen scatters light that are detected by the camera. A machine vision algorithm then identifies and tags film specimens with significant defects. Therefore, the material image analyzer system 20 is based on detecting irregularities caused when polarized light passing through the film is affected by certain physical defects. Because the material image analyzer relies on polarization of light, when the material to be tested is changed, the polarization may also change which would potentially indicate a defect to be present where there is none. However, as part of the analysis aspect, defect or irregularity analysis is shifted to the data interpretation and is conducted by looking at the range of results from a film specimen and identifying the outliers based on standard deviation and distance from the mean. Therefore, the present method of determining defects is independent of the material and is a more universal solution to the problem.

Although the material image analyzer system 20 is disclosed herein as based on the principle of polarized light, the material image analyzer system 20 may take other forms. For example, the material image analyzer system 20 may be a gel tester which quantitates and identifies the types of defects, such as an optical control system (OCS) tester. Alternatives such as optical light transmittance analyzer systems or ultrasound defect detection systems can be used. Additionally, the film specimen may skip the material image analyzer system 20 and proceed, in any order, to any of the mentioned systems, such as the thickness measurement system 16, the cutting device 18, or the tear analysis device 22. In this situation, or in addition to use of the material image analyzer system 20, the film specimen can be tested with the tear analysis device multiple times to achieve a statistical model which could be used to identify film specimens that may have defects.

Figure 12:
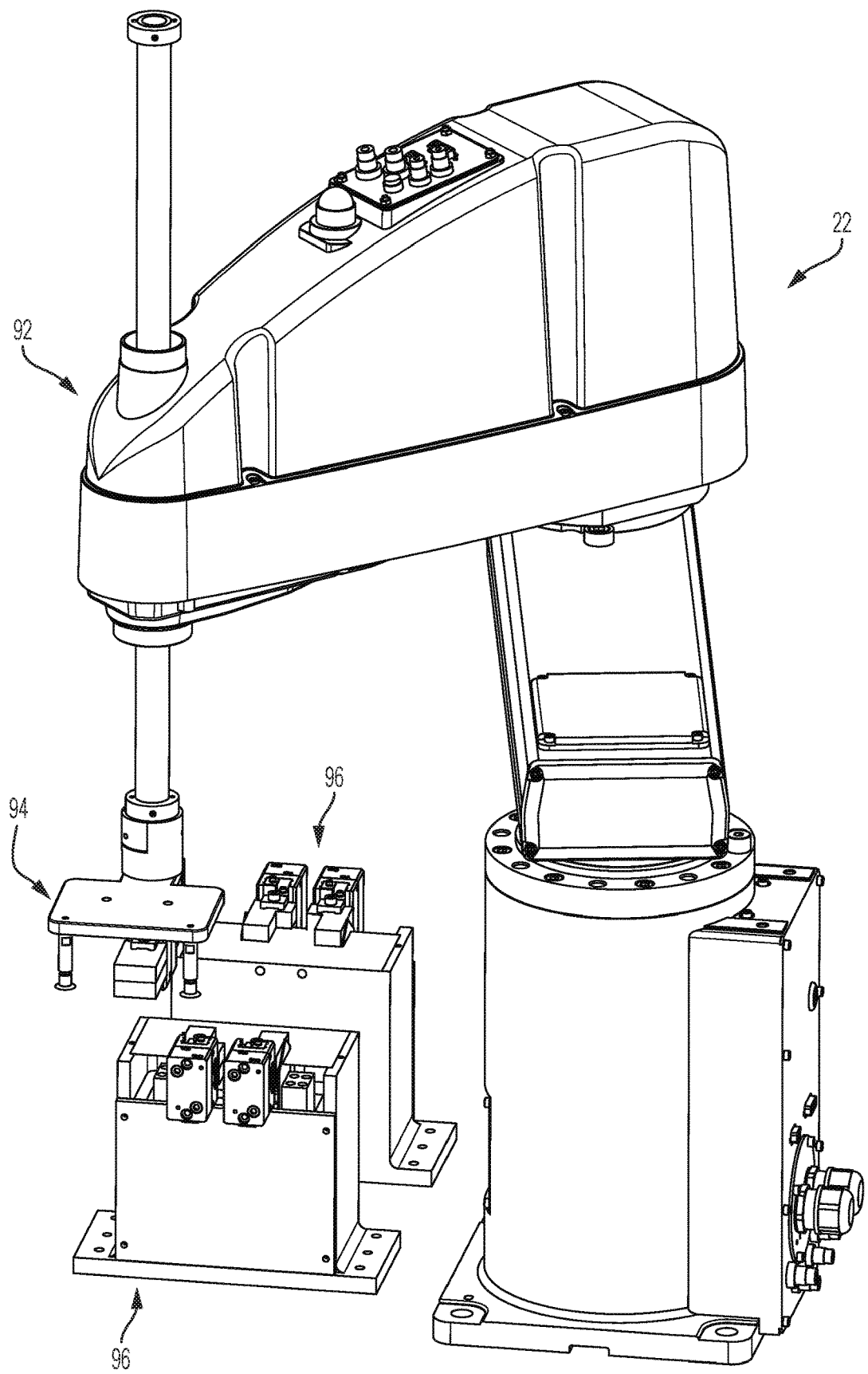
FIG. 12 shows a three-dimensional perspective view of a fixed clamp station and a robotic clamp, according to an embodiment of the present disclosure.

Following material image analyzer system 20, the film specimen is moved by the robotic system 12 to the tear analysis device 22. The tear analysis device 22 tears the film specimen at a predetermined speed and acceleration. A load cell measures the force profile throughout the tear of the film specimen. FIG. 12 shows a three-dimensional perspective view of the tear analysis device 22, according to an embodiment of the present disclosure. The tear analysis device 22 may include a tear robot 92 attached to a movable clamp, such as a robotic clamp 94. The tear analysis device 22 may include a fixed clamp station 96. The tear analysis device 22 may include a second fixed clamp station 96 located opposite the first fixed clamp station 96. The tear analysis device 22 may include more or less than the two fixed clamp stations 96 shown in FIG. 12.

Figure 13A:
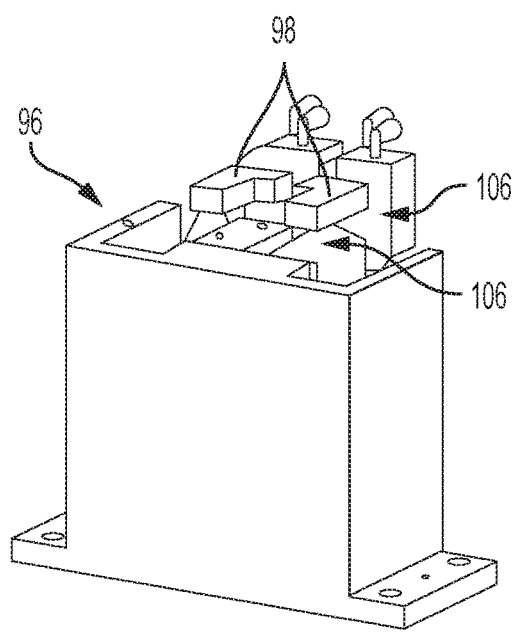
FIGS. 13A to 13C show three-dimensional perspective views of a fixed clamp station of a tear analysis device, according to an embodiment of the present disclosure.
Figure 13B:
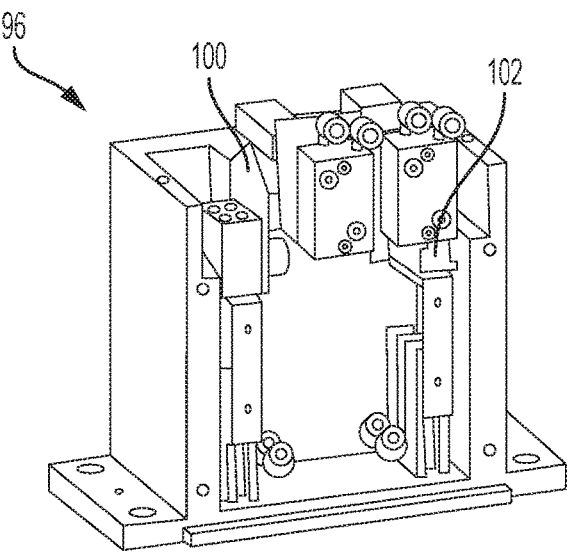
Figure 13C:
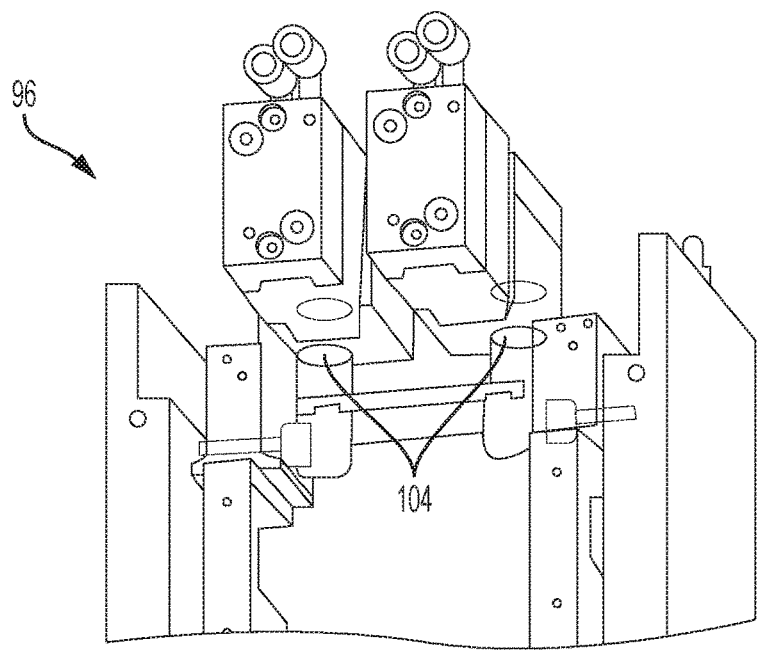

FIGS. 13A-13C show a three-dimensional perspective view of the fixed clamp station 96, according to an embodiment of the present disclosure. The fixed clamp station 96 is capable of holding two film specimens, such as two of the 3"×3" (76 mm×76 mm) film specimens cut by the cutting device 18. A second fixed clamp station 96 may be provided opposite of the fixed clamp station 96 to accommodate two additional film specimens, such as the remaining two 3"×3" (76 mm×76 mm) film specimens cut by the cutting device 18. Each fixed clamp station 96 may include a fixed clamp gripper 98, a slitter blade 100, a slitter blade actuator 102, and a load cell 104. Although the fixed clamp stations 96 are described with relation to four 3"×3" (76 mm×76 mm) specimens, it is to be understood that more or less specimens of different shapes and sizes may be tested. That is, the specimen need not be 3"×3" (76 mm×76 mm), but could be any size, shape, or quantity.

Referring to FIG. 13A, two fixed clamp grippers 98 are shown. The fixed clamp grippers 98 may each include two gripper fingers 106 that are pneumatically operated. The fixed clamp grippers 98 may be Schunk MPG50 grippers. Each fixed clamp gripper 98 may clamp a single film specimen 68 (see, e.g., FIG. 7) between the gripper fingers 106. The lower gripper finger 106 may be mounted on top of the load cell 104. According to an embodiment, the load cell 104 may be the only point of support between the fixed clamp gripper 98 and the rest of the fixed clamp station 96. Such an arrangement allows the load cell 104 to accurately measure the tear force via the fixed clamp gripper 98.

Referring to FIG. 13B, two slitter blades 100 and slitter blade actuators 102 are shown. The slitter blade actuators 102 drive the slitter blades 100 to cut a film specimen to allow for initiation of the tear propagation. The slitter blade actuator 102 may actuate the slitter blade 100 between a retracted (not depicted) and extended position (FIG. 13B). In the retracted position, the slitter blade 100 may not extend past the top surface of the lower gripper finger 106. In the extended position, the slitter blade 100 may extend upward, past the top surface of the lower gripper finger 106 such that it initiates a cut into the film specimen gripped between the lower gripper finger 106 and upper gripper finger 106. The slitter blade actuator 102 may be operated pneumatically in a linear direction along the vertical axis of the fixed clamp station 96. The slitter blade actuator 102 may alternatively be a hydraulic, electric, mechanical, magnetic, thermal, or other known actuation device. As depicted, the fixed clamp station 96 has two slitter blades 100 and slitter blade actuators 102 to perform an initial cut in two 3"×3" (76 mm×76 mm) film specimens, however, other dimensions are possible. Although the slitter blade 100 is described and depicted as coupled to the fixed clamp station 96, it is understood that the slitter blade 100 may be provided on other components which locate the slitter blade between the gripper fingers of the fixed clamp gripper 98.

Referring to FIG. 13C, two load cells 104 are shown. Each load cell 104 may be mounted such that the bottom face of the load cell 104 is mounted to the fixed clamp station 96. A gripper finger 106 may be mounted on the top face of the load cell 104. This allows the fixed clamp gripper 98 to have a pulling action on the load cell 104 during the tearing of the film specimen and the load cell 104 thus measures the tension force. The load cell 104 may be a six axis load cell or a single axis load cell. An exemplary six axis load cell may be a FT17900, Nano 25. An exemplary single axis load cell may be an ICP Force Sensor, 208C02. Although the load cell 104 is described and depicted on the fixed clamp station 96, it is understood that the load cell 104 may be coupled to a part of the robotic clamp 94, such as a gripper finger 108.

Figure 14:
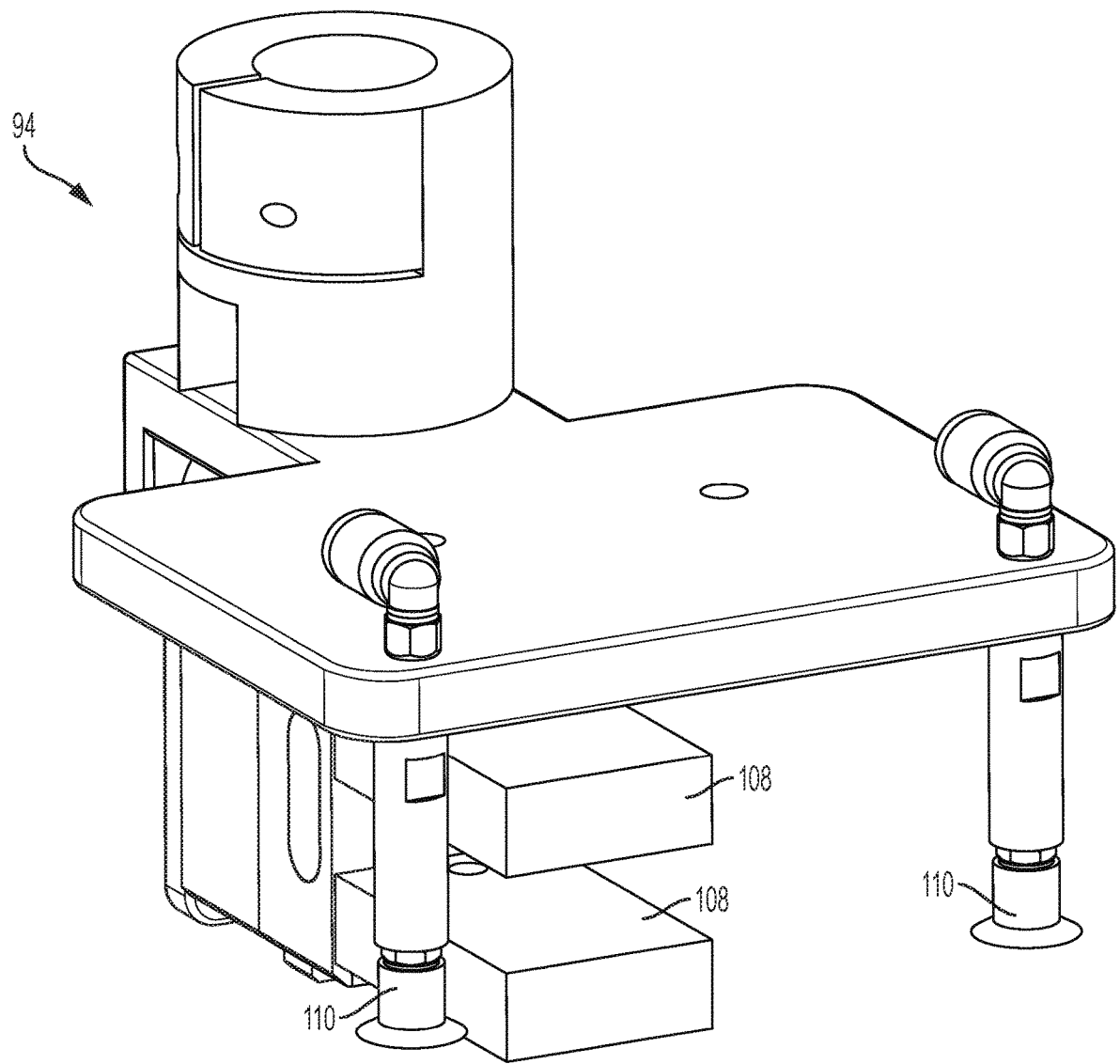
FIG. 14 shows a three-dimensional perspective view of a robotic clamp of a tear analysis device, according to an embodiment of the present disclosure.

FIG. 14 shows a three-dimensional perspective view of the robotic clamp 94, according to an embodiment of the present disclosure. The robotic clamp 94 may be mounted on a 4-axis tear robot 92 (FIG. 12), which can move in the X-Y plane and in the vertical Z-direction and rotate about the Z-axis. The tear robot 92 may be an Epson SCARA robot model G10-8545. The tear robot 92 may be any robot which is capable of movement within at least the X-Y plane to accommodate the tearing of the material sample. The robot may be any robot which can be programmed to tear the film specimen in a number of directions, for example, angular, straight, vertical, horizontal, and circular, or along a defined trajectory. In an embodiment, the robot is programmed to tear the film specimen in the vertical direction and the motion parameters for the robot are set at a maximum linear velocity of 1325 mm/s (4.4 ft/s) and acceleration of 10000 mm/s$^2$ (32.8 ft/s$^2$).

The robotic clamp 94 may include two gripper fingers 108 for holding the film specimen during the tear test. The gripper fingers 108 may be pneumatically actuated. The robotic clamp 94 may include vacuum cups 110 for collecting and dispensing of the torn film specimen after the test. Although two vacuum cups 110 are shown, any number of vacuum cups may be used to collect and dispense of the film specimen.

Figure 15:
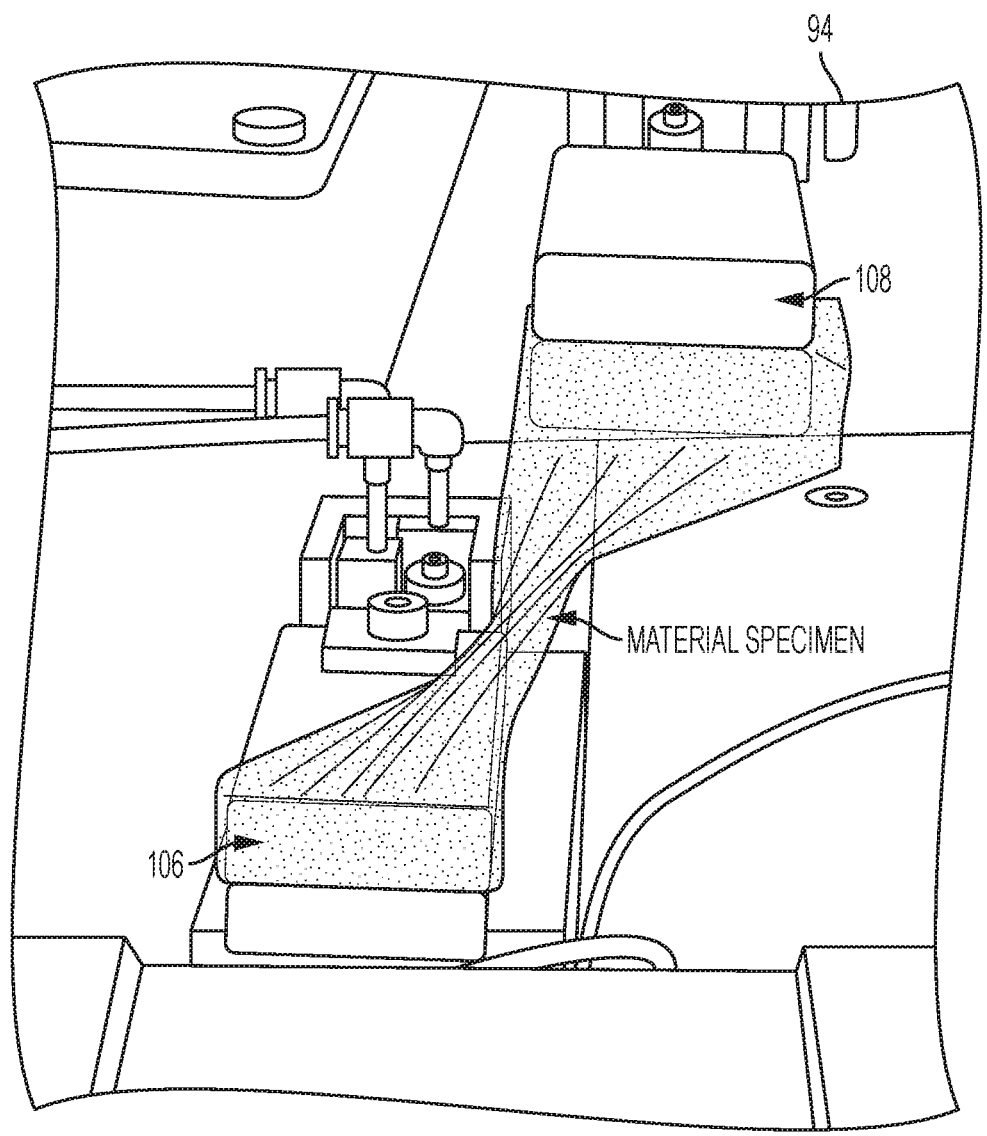
FIG. 15 shows a three-dimensional perspective view of a robotic clamp pulling a piece of film in a direction away from a fixed clamping station, according to an embodiment of the present disclosure.

Referring to FIG. 15, once the slit has been formed, the robotic clamp 94 may be moved in an upward, vertical motion by the tear robot 92. This motion may propagate a tear along the slit, such that the film specimen is torn in a first portion and a second portion. The first portion may be gripped by the gripper fingers 108 of robotic clamp 94 and the second portion may be gripped by the fixed gripper fingers 106 of the fixed clamp stations 96. The force profile is measured during the tear with the load cell 104, and processed/stored by the computer system 26.

Referring back to FIG. 1, the testing procedure for the embodiment of the tear analysis system 10 may include the following steps:
  (a) picking up a film sample by the robotic system 12 using the material holder system 14,
  (b) measuring a thickness of the film sample using the thickness measurement system 16,
  (c) cutting the 6"×6" (152 mm×152 mm) film sample into four 3"×3" (76 mm×76 mm) film specimens using the cutting device 18,
  (d) placing the four 3"×3" (76 mm×76 mm) film specimens into the tear analysis device 22, and
  (e) tearing the four 3"×3" (76 mm×76 mm) film specimens and respectively, measuring force profiles, and disposing of the tested film specimens.
  (f) Optionally, the testing procedure may include performing a material image defect analysis of the film specimens using the material image analyzer system 20.

With respect to step (a), a 6"×6" (152 mm×152 mm) film sample is transported to a work surface 24 via a transport system. The film sample can have a sample identification to associate the resultant test data (e.g., from the thickness measurement system 16, material image analyzer system 20, and tear analysis device 22) with the sample, for example, a Library ID and/or a file naming convention. The robotic system 12 moves the material holder system 14 near the film sample on the transport system. With the vacuum cups 44 (or other known gripping devices) facing in a downward direction, the 6"×6" (152 mm×152 mm) film sample is gripped with the vacuum cups 44, such that the material holder system 14 and vacuum cups 44 are located above the film sample.

With respect to step (b), the robotic system 12 may move the material holder system 14, which is holding the film sample, to the thickness measurement system 16. The robotic system 12 may locate the film sample between the contact surfaces 46 and 48 of the thickness measurement system 16. The shafts 54 linked to contact surfaces 46 are extended to measure the thickness of the film.

With respect to step (c), the robotic system 12 with the gripped film sample is moved from the thickness measurement system 16 to the cutting device 18. The cutting device 18 cuts the film sample into smaller film specimens. For example, a 6"×"6" (152 mm×152 mm) film sample can be cut into four film specimens sized 3"×3" (76 mm×76 mm), however other sizes and quantities are possible.

The gripped film sample is rotated such that the vacuum cups 44 and material holder system 14 are now located beneath the film sample and the film sample is inserted between the film support plate 56 and pressure plate 62 of the cutting device 18. The film sample is gripped with the vacuum cups 82 on the pressure plate 62 and the vacuum cups 44 of the material holder system 14 are released. The pressure plate 62 is lowered with pneumatic cylinder 58 such that the film sample is gripped between grooves 78 and tongues 80. The first linear motor 64 is actuated to move blade 70 to cut the film sample in a first direction. The first linear motor 64 and blade 70 are then retracted. The second linear motor 64 is actuated to move second blade 70 to cut the film sample in a second direction perpendicular to the first direction. The second linear motor 64 and blade 70 are then retracted. The 6"×6" (152 mm×152 mm) film sample is now four film specimens sized 3"×3" (76 mm×76 mm). The pressure plate 62 is raised with pneumatic cylinder 58 and the robotic system 12 moves the material holder system 14 underneath the four film specimens. The four film specimens are gripped with the vacuum cups 44 of the material holder system 14 and the vacuum cups 82 of the pressure plate 62 are released. Alternative methods of cutting film specimens from a film sample may be employed.

With respect to step (d), the robotic system 12 moves the material holder system 14, and the four film specimens held thereby, to the tear analysis device 22. The robotic system 12 locates two of the 3"×3" (76 mm×76 mm) film specimens between the gripper fingers 106 of a first fixed clamp station 96. The pneumatic operator is actuated to hold the two film specimens between the gripper fingers 106. The vacuum cups 44 are released from the first two specimens. The robotic system 12 then locates the remaining two of the 3"×3" (76 mm×76 mm) film specimens between the gripper fingers 106 of a second fixed clamp station 96 located opposite of the first fixed clamp station 96. The pneumatic operator is actuated to hold the remaining two film specimens between the gripper fingers 106. The vacuum cups 44 are released from the remaining two film specimens. The robotic system 12 moves the material holder system 14 away from the second fixed clamp station 96.

At this point, the robotic system 12 has delivered all four film specimens to the tear testing system. The robotic system 12 may now retrieve another 6"×6" (152 mm×152 mm) film sample from the transport system and begin steps (a) through (e) again while the robotic clamp 94 performs step (f), the test on the first four 3"×3" (76 mm×76 mm) film specimens. Such simultaneous or substantially simultaneous operation of the robotic system 12 and the robotic clamp 94 allows for high throughput of specimen testing.

With respect to step (e), the robotic clamp 94 is moved to grip a first of the four 3"×3" (76 mm×76 mm) film specimens, such that the film specimen is gripped by gripper fingers 108 of the robotic clamp 94 and gripper fingers 106 of the fixed clamp station 96. The slitter blade 100 is actuated to cut a slit into the first film specimen between the gripper fingers 106 and gripper fingers 108. The robotic clamp 94 is then moved in an upward, vertical motion to propagate a tear along the slit, such that the film specimen is torn into a first portion and a second portion (FIG. 15). The force profile is measured along the tear with the load cell 104. Continuing to grip the first film specimen portion with the gripper fingers 108 of the robotic clamp 94, the robotic clamp 94 is lowered and the vacuum cups 110 are actuated to grip the second film specimen portion. The gripper fingers 108 are released such that the robotic clamp 94 and vacuum cups 110 are allowed to move the first and second film specimen portions to a disposal site. The second film specimen portion held by vacuum cups 110 is moved against a disposal mechanism, such as a brush or puff of air, to dislodge the second film specimen portion from the gripper fingers or the vacuum cups 110 and fall into a disposal container. The first film specimen portion held by the gripper fingers 108 of the robotic clamp 94 is released such that the first film specimen portion may also fall into the disposal container or allow the disposal mechanism to dislodge the film.

After disposal of the first 3"×3" (76 mm×76 mm) film specimen, the robotic clamp 94 is returned to the first fixed clamp station 96 and repeats step (f) on the second 3"×3" (76 mm×76 mm) film specimen held in the first fixed clamp station 96. After disposal of the second 3"×3" (76 mm×76 mm) film specimen, the robotic clamp 94 is moved to the second fixed clamp station 96 and repeats the tear test and disposal of step (f) on the third and fourth film specimens held on the second fixed clamp station 96.

According to embodiments, and prior to any of steps (b), (c), and (d), the gripped 3"×3" (76 mm×76 mm) film specimens may be rotated such that the vacuum cups 44 and material holder system 14 are now located above the film specimens. The film specimens may be inserted into a material image analyzer system 20. The film specimens are analyzed for defects and irregularities using the material image analyzer system 20. According to embodiments, the material image analyzer system 20 can analyze one or more of the following qualities of the film specimen: the film region does not contain gross defects that will impact the results of the tear analysis; the edges of the film specimen are not jagged; and the film specimen is square (i.e. properly oriented and/or properly cut) in the material holder system 14. The step of analyzing with the material image analyzer system 20 may be omitted.

Although the process is described in the above order, it will be recognized that the order may be altered. According to embodiments, the order can be based, for example, on proximity of the components on the work surface 24 to promote efficiency of the system.

Although robotic clamp 94 is described and depicted for propagating the tear in the 3"×3" (76 mm×76 mm) film specimen, other alternatives may be employed, such as linear motors, other types of robotic systems, and/or automated picking and placing of a dead weight for gravity drop tears.

Although robotic clamp 94 is described as propagating the tear through an upward, vertical motion, other alternative trajectories may be employed. The robotic clamp 94 (or other tear propagation mechanism) may be programed to perform the tear motion in a defined trajectory, which may be linear trajectories (vertical and/or horizontal) or in angular, circular or spline trajectories. Additionally, the acceleration, velocity, and travel distance of the robotic clamp 94 may be programmed. A variable acceleration motion, such as a sinusoidal curve (e.g., acceleration curve for a pendulum) can be programmed. Alternatively, the tear robot 92 and robotic clamp 94 may be replaced with high speed linear motors capable of tearing the film specimen.

Furthermore, different types of load cells 104 can be used to measure the force profile along the tear. The type of load cell 104 chosen may depend on several factors including, the range of the load cell (which is dependent on the maximum tear strength force to be measured), the resolution of the load cell (which is based on the desired precisions and accuracy of the measurement), and the degree of force measurement of the load cell (which is dependent on the requirement for detailed tear analysis of the film specimen). A six-axis load cell can be used to measure and analyze the tear force in each of the six directions ($F_x$, $F_y$, $F_z$, $T_x$, $T_y$, $T_z$) or a single-axis load cell can be used to measure force in the direction of the tear.

Figure 16:
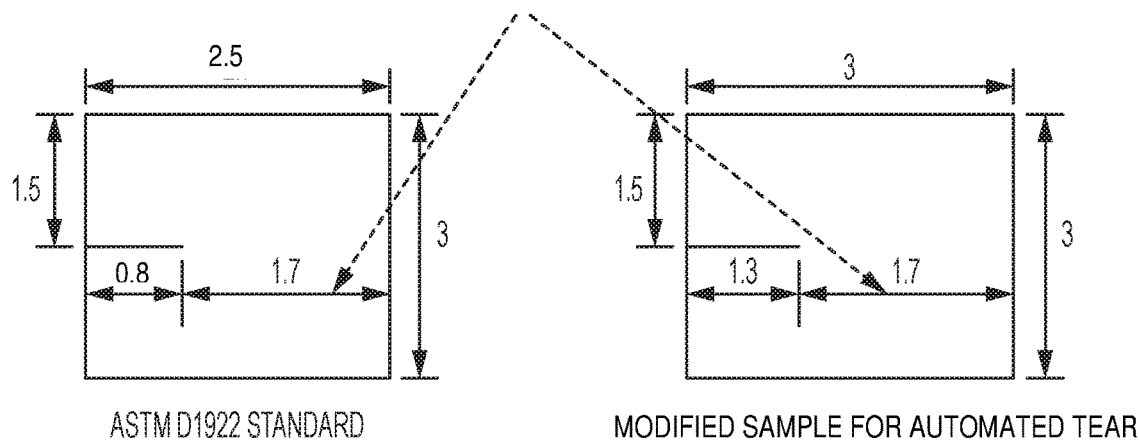
FIG. 16 shows a comparison between a standard test specimen and a modified test specimen, according to an embodiment of the present disclosure.

The equipment in the tear analysis system 10 may be used with different film specimen dimensions. Referring to FIG. 16, the tear equipment can be used for the dimensions specified in the ASTM D1922 standard, or with other dimensions such as a 3"×2.5" (76.2 mm×63.5 mm) rectangle or 3"×3" (76 mm×76 mm) square. The equipment in the tear analysis system 10 may also be used with different materials. The material may be polymer films, as described herein, or in alternate polymeric samples including adhesives, plaques, carper fibers, non-woven fibers, etc., or in non-polymeric samples such as paper, cloth, foil, etc. The tear analysis system 10 may test materials with strengths up to 4800 grams and thicknesses in the range of up to 4 mil (0.102 mm). However, stronger films can be tested. Modification to components, such as to the grippers, may also allow different materials having different dimensions, properties, characteristics, or strengths be tested.

In an embodiment, the computer system 26 in communication with the tear analysis device 22 is configured to collect or acquire data from the thickness measurement system 16, material image analyzer system 20, and the tear analysis device 22. The computer system 26 includes a user interface to allow the user to enter test parameters such as the identification of the plastic film so that the results can be stored into a database linking it to the correct identification. The user interface also allows changes to test parameters such as tear trajectory (distance, speed, and acceleration). The computer system 26 may control both the robotic system 12 and the robotic clamp 94. The robotic system 12 may run on the main controller while the robotic clamp 94 may be connected as a slave to the main controller. The data acquired with respect to the film specimen may be stored in master database on the computer system 26 or in communication with the computer system 26. The data may include thickness measurement, image analysis, force profiles, tear test data, etc.

In an embodiment, the 3"×3" (76 mm×76 mm) film specimen has the same length of tear (1.7") as in the original ASTM D1922 specimen, as seen in FIG. 16. In an embodiment, force versus time is plotted for the tear duration of the film. From this data, the peak force required to tear the film specimen is calculated:

$$F_{peak} = \max(F),$$

Figure 17:
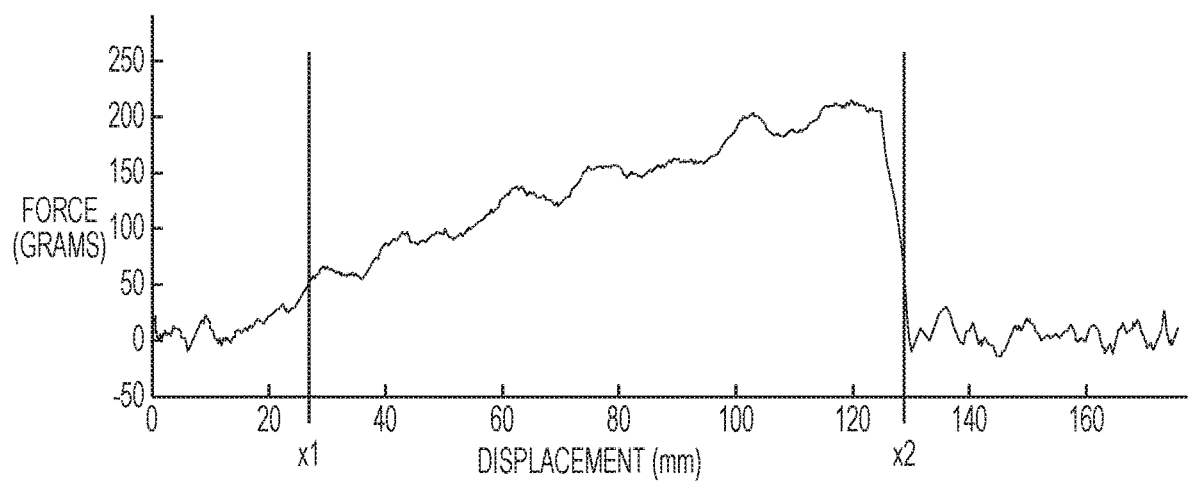
FIG. 17 shows a plot of force versus displacement, according to an embodiment of the present disclosure.
Figure 18:
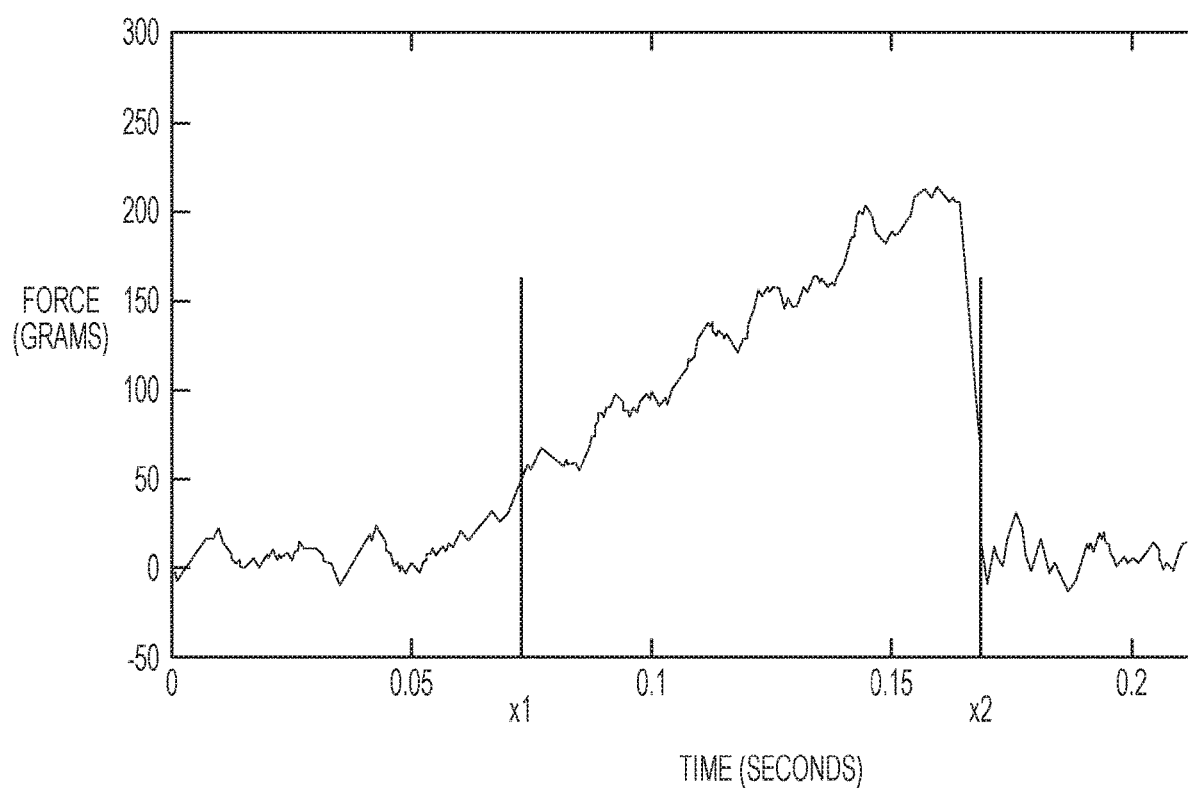
FIG. 18 shows a plot of force versus time, according to an embodiment of the present disclosure.

The work done to tear the film is calculated by integrating the force curve over the displacement ($x_2 - x_1$). An exemplary tear test is depicted in FIGS. 17 and 18. FIG. 17 depicts the force versus displacement curve for the test. FIG. 18 depicts the force versus time curve for the test. In this exemplary test, the displacement points ($x_2$, $x_1$) are selected at a force threshold of 50 grams to ensure the force integral is over the displacement distance when the specimen is tearing, however other threshold values are possible. The work done is calculated:

$$W = \int_{x1}^{x2} F(s) \cdot ds$$

The average force is computed by dividing the computed work done required to tear the film over the distance traveled in tearing the film:

$$F_{avg} = \frac{W}{s}$$

The peak force and average force are computed for each of the specimens in a sample size and the statistical parameters mean and standard deviation are computed from the sample size. The normalized value for each of the forces is computed as the force per mil thickness.

The term "computer system" is used herein to encompass any data processing system or processing unit or units. The computer system may include one or more processors or processing units. The computer system can also be a distributed computing system. The computer system may include, for example, a desktop computer, a laptop computer, a handheld computing device such as a PDA, a tablet, a smartphone, etc. A computer program product or products may be run on the computer system to accomplish the functions or operations described in the above paragraphs. The computer program product includes a computer readable medium or storage medium or media having instructions stored thereon used to program the computer system to perform the functions or operations described above. Examples of suitable storage medium or media include any type of disk including floppy disks, optical disks, DVDs, CD ROMs, magnetic optical disks, RAMs, EPROMs, EEPROMs, magnetic or optical cards, hard disk, flash card (e.g., a USB flash card), PCMCIA memory card, smart card, or other media. Alternatively, a portion or the whole computer program product can be downloaded from a remote computer or server via a network such as the internet, an ATM network, a wide area network (WAN) or a local area network.

Stored on one or more of the computer readable media, the program may include software for controlling a general purpose or specialized computer system or processor. The software also enables the computer system or processor to interact with a user via output devices such as a graphical user interface, head mounted display (HMD), etc. The software may also include, but is not limited to, device drivers, operating systems and user applications. Alternatively, instead or in addition to implementing the methods described above as computer program product(s) (e.g., as software products) embodied in a computer, the method described above can be implemented as hardware in which for example an application specific integrated circuit (ASIC) or graphics processing unit or units (GPU) can be designed to implement the method or methods, functions or operations of the present disclosure.

The invention claimed is:

1. A system for analyzing a physical characteristic of a film sample, the system comprising:

a material holder system configured to hold the film sample; and a tear analysis device configured to tear the film sample by stretching the film sample and measure a characteristic of the tear;

a cutter configured to cut the film sample into a plurality of film specimens, wherein a movable system is configured to move the film sample in the material holder system to the tear analysis device, the cutter comprises a film support plate configured to hold the film sample during cutting, and a pressure plate configured to press the film sample against the film support plate, wherein one of the film support plate and the pressure plate defines one or more tongues and the other of the film support plate and the pressure plate defines one or more grooves that mate with the one or more tongues, and wherein the film sample is held between film support plate and the pressure plate during cutting.

2. The system of claim 1, wherein the movable system comprises an articulating-arm robotic arm system.

3. The system of claim 1, wherein the movable system is configured to move the film sample to the cutter, and to move the plurality of film specimens from the cutter to at least one of a material thickness measurement system, a material image analyzer system, and the tear analysis device.

4. The system of claim 1, wherein the material holder system includes a vacuum suction system configured to hold the film sample and film specimens through vacuum suction.

5. The system of claim 1, further comprising a material thickness measurement system configured to measure a thickness of the film sample.

6. The system of claim 1, wherein the material thickness measurement system comprises a probe configured to measure a thickness of the film sample over a spread area to avoid puncturing the film sample during the measurement.

7. The system of claim 1, wherein the cutter comprises a first linear actuator in connection with a first blade for cutting the film sample in a first direction, and a second linear actuator in connection with a second blade for cutting the film sample in a second direction transverse to the first direction.

8. The system of claim 1, wherein the tear analysis device comprises:

a fixed clamp station that holds a first portion of the film sample or one of the plurality of film specimens; and a movable clamp that holds a second portion of the film sample or the one of the plurality of film specimens.

9. The system of claim 8, further comprising a robotic arm that moves the movable clamp with respect to the fixed clamp station.

10. The system of claim 8, further comprising a force sensor associated with one of the fixed clamp station and the movable clamp.

11. The system of claim 8, further comprising at least one blade configured to cut a slit in the film sample or film specimen, the at least one blade located between a gripper of the fixed clamp station and the movable clamp.

12. The system of claim 1, further comprising a material image analyzer system configured to detect a defect in the film sample.

13. A method for analyzing a physical characteristic of a film sample, the method comprising:

holding the film sample by a material holder system connected to a movable system;

moving the film sample by the movable system to a cutter;

cutting the film sample into at least two smaller film species using the cutter;

moving the film sample using the movable system to a tear analysis device; and tearing the film sample by stretching the film sample and measuring a characteristic of the tear using the tear analysis device;

wherein the cutter comprises a film support plate configured to hold the film sample during cutting and a pressure plate configured to press the film sample against the film support plate, wherein one of the film support plate and the pressure plate defines one or more tongues, and wherein the film sample is held between the film support plate and the pressure plate during cutting.

14. The method of claim 13, wherein testing the physical characteristic of the film sample comprises:

holding a first portion of the film sample or film specimen using a fixed clamp;

holding a second portion of the film sample film specimen using a movable arm; and moving the movable arm to tear the film sample or film specimen.

15. The method of claim 14, further comprising cutting a slit in the film sample or the film specimen between the first portion and the second portion using a slitter blade.

16. The method of claim 13, further comprising:

moving the film sample by the movable system to a material thickness measurement system; and measuring a thickness of the film sample using the material thickness measurement system.

17. The method of claim 13, further comprising:

moving the film sample by the movable system to a material image analyzer system; and detecting a defect in the film sample using the material image analyzer system.

* * * * *